US010981980B2

(12) United States Patent
Hall et al.

(10) Patent No.: US 10,981,980 B2
(45) Date of Patent: Apr. 20, 2021

(54) POLYPEPTIDE TARGETING APTAMERS FOR CHARACTERIZATION, CAPTURE, AND CLINICAL MANAGEMENT OF CIRCULATING TUMOR CELLS

(71) Applicant: Counterpoint Biomedica LLC, Santa Monica, CA (US)

(72) Inventors: Frederick L. Hall, Laguna Niguel, CA (US); Erlinda M. Gordon, Carmel, CA (US)

(73) Assignee: Counterpoint Biomedica LLC, Santa Monica, CA (US)

( * ) Notice: Subject to any disclaimer, the term of this patent is extended or adjusted under 35 U.S.C. 154(b) by 0 days.

(21) Appl. No.: 16/310,271

(22) PCT Filed: Jun. 9, 2017

(86) PCT No.: PCT/US2017/036853
§ 371 (c)(1),
(2) Date: Dec. 14, 2018

(87) PCT Pub. No.: WO2017/218355
PCT Pub. Date: Dec. 21, 2017

(65) Prior Publication Data
US 2019/0211088 A1    Jul. 11, 2019

Related U.S. Application Data

(60) Provisional application No. 62/350,683, filed on Jun. 15, 2016.

(51) Int. Cl.
| | | |
|---|---|---|
| *C07K 16/18* | (2006.01) |
| *A61K 38/00* | (2006.01) |
| *A61K 47/60* | (2017.01) |
| *A61P 31/12* | (2006.01) |
| *A61P 35/00* | (2006.01) |
| *A61K 38/39* | (2006.01) |
| *A61K 39/395* | (2006.01) |
| *A61K 49/00* | (2006.01) |
| *A61M 1/36* | (2006.01) |
| *B01D 15/34* | (2006.01) |
| *B01D 15/38* | (2006.01) |
| *B01J 20/281* | (2006.01) |
| *C07K 14/78* | (2006.01) |
| *C07K 16/22* | (2006.01) |
| *C12N 5/09* | (2010.01) |
| *G01N 30/84* | (2006.01) |
| *G01N 33/50* | (2006.01) |
| *G01N 33/574* | (2006.01) |
| *G01N 30/00* | (2006.01) |

(52) U.S. Cl.
CPC ............ *C07K 16/18* (2013.01); *A61K 38/00* (2013.01); *A61K 38/39* (2013.01); *A61K 39/3955* (2013.01); *A61K 47/60* (2017.08); *A61K 49/0004* (2013.01); *A61M 1/3687* (2013.01); *A61P 31/12* (2018.01); *A61P 35/00* (2018.01); *B01D 15/34* (2013.01); *B01D 15/3809* (2013.01); *B01J 20/281* (2013.01); *C07K 14/78* (2013.01); *C07K 16/22* (2013.01); *C12N 5/0693* (2013.01); *G01N 30/482* (2013.01); *G01N 30/84* (2013.01); *G01N 33/5011* (2013.01); *G01N 33/5091* (2013.01); *G01N 33/57492* (2013.01); *C07K 2317/92* (2013.01); *C07K 2319/21* (2013.01); *C07K 2319/24* (2013.01); *C07K 2319/40* (2013.01); *G01N 2030/484* (2013.01)

(58) Field of Classification Search
CPC combination set(s) only.
See application file for complete search history.

(56) References Cited

U.S. PATENT DOCUMENTS

| 4,966,848 | A | * | 10/1990 | Smith | .................. | C12N 9/1029 |
| | | | | | | 435/193 |
| 5,223,421 | A | * | 6/1993 | Smith | .................. | C12N 9/1029 |
| | | | | | | 435/193 |
| 5,837,218 | A | * | 11/1998 | Peers | .................. | A61K 51/088 |
| | | | | | | 424/1.69 |
| 6,387,663 | B1 | | 5/2002 | Hall et al. |
| 6,468,798 | B1 | | 10/2002 | Debs et al. |
| 6,503,713 | B1 | | 1/2003 | Rana |
| 7,972,779 | B2 | | 7/2011 | Caspi et al. |
| 2012/0208770 | A1 | | 8/2012 | Li et al. |

FOREIGN PATENT DOCUMENTS

WO    WO 2016/054107    4/2016

OTHER PUBLICATIONS

Delgado C, Francis GE, Fisher D., "The uses and properties of PEG-linked proteins," Crit Rev Ther Drug Carrier Syst. 1992;9(3-4): 249-304 (Year: 1992).*

(Continued)

*Primary Examiner* — Thomas S Heard
(74) *Attorney, Agent, or Firm* — Fish & Richardson P.C.

(57) ABSTRACT

Provided herein are new compositions and methods to target and deliver agents to pathological areas by utilizing multi-functional compounds. These compounds include three or more domains: (i) a vimentin-binding peptide, (ii) a linker, and (iii) a drug binding, a capturing reagent, or a detectable moiety. These compounds can be used to detect, isolate, and/or treat cancerous cells such as circulating tumor cells.

10 Claims, 8 Drawing Sheets
Specification includes a Sequence Listing.

(56) References Cited

OTHER PUBLICATIONS

Bhattacharya et al, "Interaction between Bluetongue virus outer capsid protein VP2 and vimentin is necessary for virus egress," Virol J., 2007, 12 pages.
Chaffer & Weinberg, "A perspective on cancer cell metastasis," Science, 2011, 331:1559-1564.
Chawla et al, Advanced Phase I/II Studies of Targeted Gene Delivery In Vivo: Intravenous Rexin-G for Gemcitabine-resistant Metastatic Pancreatic Cancer, Mol Ther, 2010, 18:435-441.
Chawla et al., "Phase I/II and Phase II Studies of Targeted Gene Delivery In Vivo: Intravenous Rexin-G for Chemotherapy-resistant Sarcoma and Osteosarcoma," Mol Ther, 2009, 17(9):1651-7.
Chen et al, "Fusion Protein Linkers: Property, Design and Functionality," Adv Drug Deliv Rev., Oct. 15, 2013, 65(10):1357-1369.
Chichili et al., "Linkers in the structural biology of protein-protein interactions," Protein Science, 2013, 22:153-167.
Colberre-Garapin et al, "A New Dominant Hybrid Selective Marker for Higher Eukaryotic Cells," J. Mol. Biol., 1981, 150:1.
Cruz et al, "Interaction of the von Willebrand Factor (vWF) with Collagen," J. Biol. Chem, May 5, 1995, 270:10822-10827.
Czarnik, "Encoding methods for combinatorial chemistry," Curr. Opin. Chem. Bio., 1997, 1:60-66.
Dave et al, "Epithelial—mesenchymal transition, cancer stem cells and treatment resistance," Breast Cancer Res., 2012, 14:202-207.
Fang et al, "Collagen as a double-edged sword in tumor progression," Tumor Biol., 2014, 35:2871-2882.
Ginsburg & Bowie, "Molecular Genetics of von Willebrand Disease," Blood, 1992, 79:2507-2519.
Gordon et al, "Capture and expansion of bone marrow-derived mesenchymal progenitor cells with a transforming growth fact-β1-von Willebrand's factor fusion protein for retrovirus-mediated delivery of coagulation factor IX," Hum. Gene Ther., Jul. 20, 1997, 8:1385-1394.
Gordon et al., "Inhibition of Metastatic Tumor Growth in Nude Mice by Portal Vein Infusions of Matrix-targeted Retroviral Vectors Bearing a Cytocidal Cyclin G1 Construct," Cancer Res., Jul. 1, 2000, 60:3343-3347.
Gordon et al., Noteworthy clinical case studies in cancer gene therapy: Tumortargeted Rexin-G advances as an efficacious anticancer agent Int'l J Oncol., 2010, 36:1341-1353.
Gordon et al., "Rexin-G, a targeted genetic medicine for cancer," Expert Opin Biol Ther., 2010, 10:819-832.
Gorges et al. Circulating tumour cells escape from EpCAM based detection due to epithelial-to-mesenchymal transition. BMC Cancer 2012, 12:178-191.
Hall et al, "Molecular Engineering of Matrix-Targeted Retroviral Vectors Incorporating a Surveillance Function Inherent in von Willebrand Factor," Human Gene Therapy, May 1, 2000, 11:983-993.
Hall et al., "Design, expression, and renaturation of a lesion-targeted recombinant epidermal growth factor-von Willebrand factor fusion protein: efficacy in an animal model of experimental colitis," Intl J Mol Med, 2000, 6:635-643.
Hanahan and Weinberg, "Hallmarks of Cancer: the next generation," Cell, 2011, 144:646-674.
Hartman & Mulligan, "Two dominant-acting selectable markers for gene transfer studies in mammalian cells," Proc. Natl. Acad. Sci. USA, Nov. 1988, 85:8047-8051.
Heerboth et al., "EMT and tumor metastasis," Clinical and Translational Medicine, 2015, 4:1-13.
Horn and Sticht, "Synthetic Protein Scaffolds Based on Peptide Motifs and Cognate Adaptor Domains for Improving Metabolic Productivity," Frontiers in Bioengineering and Biotechnology, Nov. 2015, vol. 3, Article 191.
Hoylaerts et al., "von Willebrand factor binds to native collagen VI primarily via its A1 domain,". Biochem. J., 1997, 324:185-191.
Jiang et al, "Conserved structural elements in the V3 crown of HIV-1 120," Nature Structural & Molecular Biology, Aug. 2010, 17, 955-961.

Kratz, "Albumin as a drug carrier: design of prodrugs, drug conjugates and nanoparticles," Controlled Release, 2008, 132:171-83.
Kwon et al, "Analysis on the current status of targeted drug delivery to tumors," J. Controlled Release, 2012, 164:108-14.
Lankhof, H., et al., "A3 domain is essential for interaction of von Willebrand factor with collagen type III" Thrombos Haemostas, Thrombos Haemostas, 75:950-958, 1996.
Lowy et al, "Isolation of transforming DNA: cloning the hamster aprt gene," Cell, 1980, 22:817.
Lu et al., "Isolation of circulating epithelial and tumor progenitor cells with an invasive phenotype from breast cancer patients," Int J Cancer. 2010, 126: 669-683.
Lux et al, "Nanogels from Metal-Chelating Crosslinkers as Versatile Platforms Applied to Copper-64 PET Imaging of Tumors and Metastases," Theranostics, 2015, 5:277-288.
Magdesian et al, Infection by Trypanosoma cruzi Identification of a Parasite Ligand and Its Host Cell Receptor The Journal of Biological Chemistry, Mar. 7, 2001.
Maier et al, "Real-time analysis of epithelial-mesenchymal transition using fluoresecent single-domain antibodies," Sci Rep, 2015, 5:13402, 13 pages.
Miele et al., "Albumin-bound formulation of paclitaxel (Abraxane® ABI-007) in the treatment of breast cancer," Int. Journal of Nanomedicine, 2009, 4:99-105.
Mierke et al, "Integrin a-5b-1 facilitates cancer cell invasion through enhanced contractile forces," J. Cell Science, 2010, 124:369-383.
Mulligan & Berg, "Selection for animal cells that express the *Escherichia coli* gene coding for xanthine-guanine phosphoribosyltransferase," Proc. Natl. Acad. Sci. USA, Apr. 1981, 78:2072-2076.
O'Hare et al, "Transformation of mouse fibroblasts to methotrexate resistance by a recombinant plasmid expressing a prokaryotic dihydrofolate reductase," Proc. Natl. Acad. Sci. USA, 1981, 78:1527-1531.
Park, "Albumin: A Versatile carrier for drug delivery," Controlled. Release, 2012, 157:3.
Patel and Chen, "Cancer stem cells, tumor dormancy,and metastasis," Frontiers in Endocrin. 2012, 5 pages.
Pietrasa & Ostmanb, "Hallmarks of cancer: interactions with the tumor stroma," Exp. Cell Res., 2010, 313:1324-1331.
Quinlan et al, "Albumin: Biochemical Properties and Theerapeutic Potential," Hepatology, 2005, 41:1211-1219.
Santerre et al, "Expression of prokaryotic genes for hygromycin B and G418 resistance as dominant-selection markers in mouse L cells," Gene, 1984, 30:147-156.
Satelli & Li, "Vimentin, an overview and its potential as a molecular target for cancer therapy," Cell Mol Life Sci., 2011, 68:3033-3046.
Satelli et al, "Epithelial—mesenchymal transitioned circulating tumor cells capture for detecting tumor progression," Clin Cancer Res, 2014, 21:1-8.
Schneck et al, "EpCAM-Independent Enrichment of Circulating Tumor Cells in Metastatic Breast Cancer," Plos One, 2015, 23 pages.
Sirpada & Dayaraj, "Viral interactions with intermediate filaments: Paths less explored," Cell Health and Cytoskeleton, Mar. 23, 2010, 2010:2:1-7.
Szybalska & Szybalski, "Genetics of Human Cell Lines, IV. DNA-Mediated Heritable Transformation of a Biochemical Trait," Proc. Natl. Acad. Sci. USA, 1962, 48:2026.
Takagi et al, "A Collagen/Gelatin-Binding Decapeptide Derived from Bovine Propolypeptide of von Willebrand Factor," Biochemistry, 1992, 32:8530-4.
Talbot et al, "Epithelial-mesenchymal transition, the tumor microenvironment, and metastatic behavior of epithelial malignancies," Int J Biochem Mol Biol., 2012, 3:117-136.
Teixeira et al, "TrypanosomacruziBindstoCytokeratin throughConservedPeptideMotifsFoundin theLaminin-G-LikeDomainofthegp85/ Trans-sialidaseProteins," PLOS Neglected Tropical Diseases,. Sep. 23, 2015, 22 pages.
Thiery, "Epithelial-mesenchymal transitions in tumor progression,"Nature Reviews, 2002, 2:442-454.

(56) References Cited

OTHER PUBLICATIONS

Thomas et al, "Anti-idiotypic Antibody to the V3 Domain of gp120 Binds to Vimentin: A Possible Role of Intermediate Filaments in the Early Steps of HIV-1 Infection Cycle," Viral Immunol., 1996, 9(2):73-87.

Tuan et al, "Engineering, Expression and Renaturation of Targeted TGF-Beta Fusion Proteins," Conn. Tiss. Res., 1996, 34:1-9.

Valiathan et al, "Discoidin domain receptor tyrosine kinases new players in cancer progression," Cancer Metastasis Rev., 2012, 31:295-321.

Waehler et al, "Engineering targeted viral vectors for gene therapy," Nature Reviews Genetics, 2007, 8:573-587.

Wagner, "Cell Biology of Von Willebrand Factor," Ann. Rev. Cell. Biol., 1990, 6:217-246.

Wigler et al, "Transfer of Purified Herpes Virus Thymidine Kinase Gene to Cultured Mouse Cells," Cell, 1977, 11:223-232.

Wigler et al, "Transformation of mammalian cells with an amplifiable dominant-acting gene," Proc. Natl. Acad. Sci USA, Jun. 1980, 77:3567-3570.

\* cited by examiner

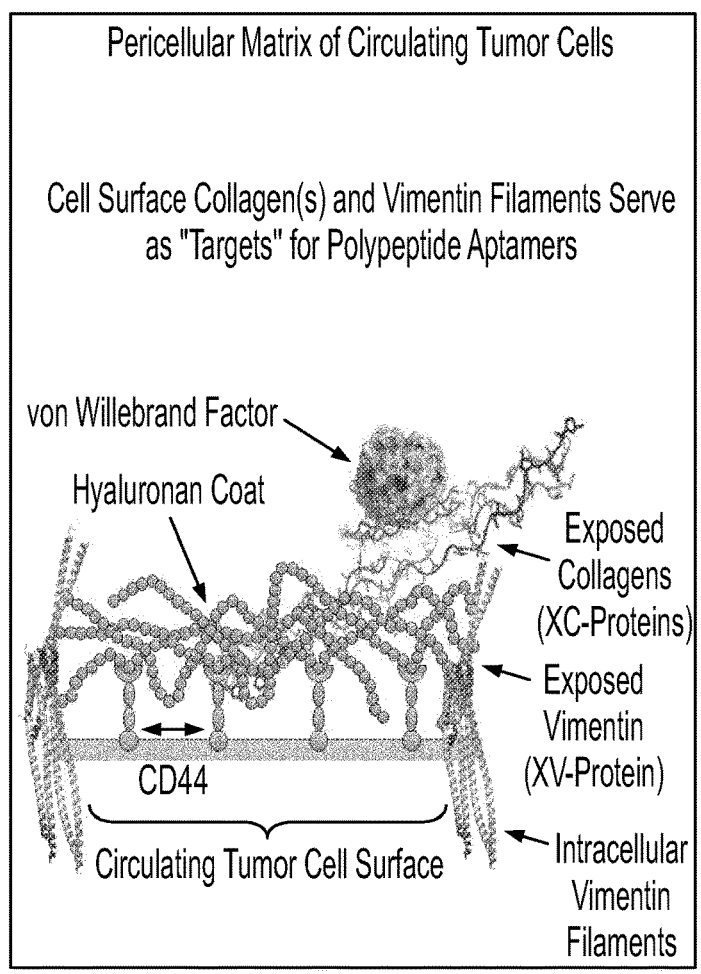
FIG. 1A
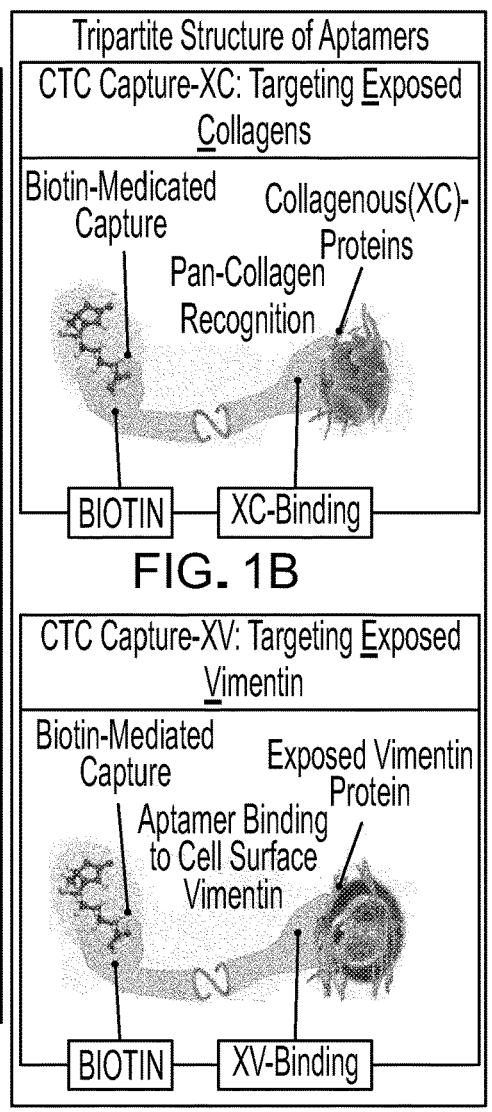
FIG. 1B
FIG. 1C
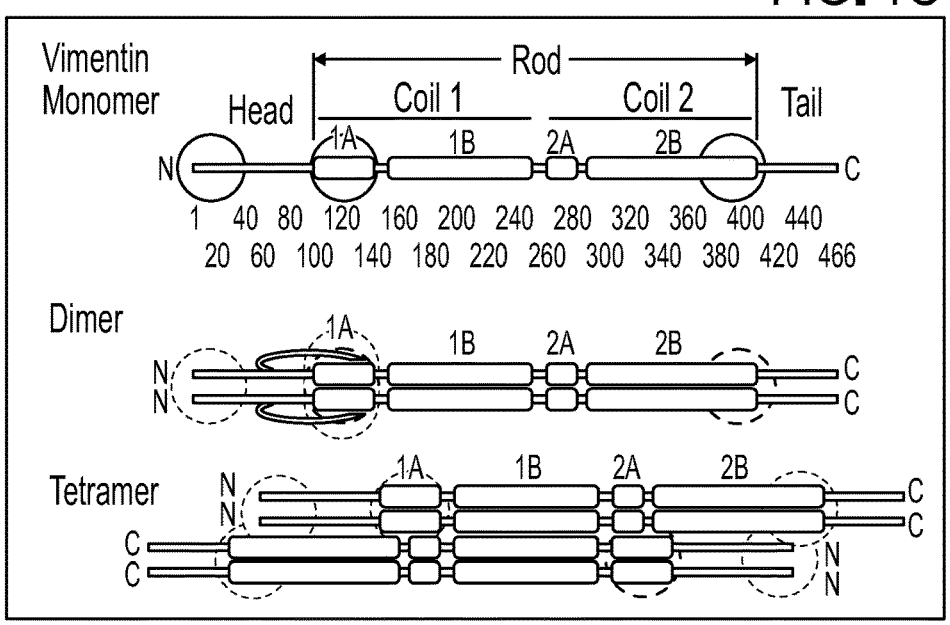
FIG. 2

1.0: L2 Linker Sequence
   RAb-VL2-282: vim-282-304
       CGKN<u>LQEAEEWY</u>KSKFADLSEAANR  -amide   25-mer 2.0: 2B(NT)-Rod Domain
   RAb-V2BN-299: vim-299-321
       CGSEAANRNNDALRQAKQESTEYRR  -amide   25-mer 3.0: C-Terminal Tail Domain
   RAb-VCT-445: vim-445-466
       CGGKTVETRDGQVINETSQHHDDLE - free acid   25-mer 4.0: 2B(CT)-Rod Domain
   Rab-V2BCT-390: vim-390-412
       KMALDIEIATYRKLLEGEESRISGC  - Conjugate via C-terminal Cys;  25-mer

US 10,981,980 B2

POLYPEPTIDE TARGETING APTAMERS FOR CHARACTERIZATION, CAPTURE, AND CLINICAL MANAGEMENT OF CIRCULATING TUMOR CELLS

CROSS-REFERENCE TO RELATED APPLICATIONS

This application is a U.S. National Phase Application under 35 U.S.C. § 371 of International Patent Application No. PCT/US2017/036853, filed on Jun. 9, 2017, which claims the benefit of prior U.S. Provisional Application Ser. No. 62/350,683, filed Jun. 15, 2016. The disclosure of the above applications are hereby incorporated by reference in their entireties.

TECHNICAL FIELD

This invention relates to new compositions and methods capable of selective and efficient targeting of pharmaceutical agents, detectable moieties, and capturing agents to pathological areas such as circulating tumor cells.

BACKGROUND

Cancer is the second most common cause of death in the US, claiming 580,000 Americans per year, more than 1,500 people each day. The number of new cancer patients diagnosed in 2012 was over 1.6 million in the U.S. alone, not including patients with noninvasive cancers and/or skin cancers. The National Institutes of Health (NIH) estimated the overall annual costs of cancer care at more than $227 billion (in 2007): including $89 billion for direct medical costs. Sales of cancer drugs in general doubled between 2005 and 2010, with conservative growth estimates of 8 to 10% per year, reaching $93 billion by 2016. Much of the overall healthcare costs of treating cancer are derived from management of the deleterious side effects of radiation and conventional chemotherapy. Nonetheless, the chemotherapy market is currently the fastest growing segment of the pharmaceutical industry, with recent estimates topping $50 billion (in 2012) and rising. Likewise, the global market for therapeutic antibodies (targeted biologics) is estimated to rise from $40 billion to $58 billion by the year 2016. However, these current cancer therapies, including surgery, systemic chemotherapy, radiation therapy, risk factor modification, are often clinically insufficient and/or unacceptably toxic. The systemic toxicities of many FDA-approved chemotherapeutic agents are a result of the non-specific distribution of these cytocidal agents in the body, which kills both cancer cells and normal cells and negatively impacts the treatment regimen and patient outcome.

As a cancer progresses from a low-grade cancer to high-grade malignant cancers, the cancer cells acquire characteristics that lead to an increase in motile "fibroid" morphology, invasiveness, resistance to apoptosis, and an increase in extracellular matrix components. Epithelioid cancer cells tend to undergo an epithelial-to-mesenchymal transition (EMT) (Thiery, Epithelial-mesenchymal transitions in tumor progression. Nature Reviews, 2002, 2:442-454; and Talbot et al., Epithelial-mesenchymal transition, the tumor microenvironment, and metastatic behavior of epithelial malignancies, Int J Biochem Mol Biol. 2012, 3:117-136) and primary cancers shed circulating tumor cells (CTCs) into the peripheral circulation. This progression of cancer cells to more-aggressive, treatment-resistant phenotypes presents a challenge for diagnostics, treatments, patient monitoring, and prognosis.

SUMMARY

The present disclosure is based, at least in part, on the development of new compounds that include at least three functional domains: (i) a peptide that binds to vimentin proteins, (ii) a linker, and (iii) a detectable moiety, a capture reagent, or a drug binding domain. These compounds enable selective and efficient targeting of chemotherapeutic agents, detectable moieties, capturing reagents, and other biological agents to not only abnormal, diseased, or degenerative tissues such as tumors, but also circulating tumor cells (CTCs). The targeted delivery is achieved by combining a vimentin-binding peptide domain with a drug-binding domain, a detectable moiety, or a capture reagent. When the vimentin-binding peptide is linked with the drug-binding domain, these targeted compounds can reduce systemic toxicity and side effects by sequestering the drugs in the tumor or cancer cell microenvironment and sparing normal cells and tissues form the toxicity of the drugs. When linked with the detectable moiety, these compounds allow for detection of cancerous tissues in vitro, ex vivo and in vivo, allowing for efficient prognosis and diagnosis of diseases. Further, when the vimentin-binding peptide is linked to a capture reagent, the compounds provide a selective method for isolating or removing cancerous cells from a sample. This isolation is helpful in acquiring CTCs for characterization and the removal is helpful for depleting CTCs from circulation of a subject suffering from metastatic cancer. These compounds can also include collagen-binding peptides to target cancer cells; linker segments to decrease steric hindrances; and/or flanking sequences to improve the functionality, pharmacokinetics, stability, and/or pharmacodynamics of the targeted compounds.

In one aspect, the present disclosure provides for a compound comprising, consisting essentially of, or consisting of: a first domain comprising a vimentin-binding peptide; a second domain comprising a linker; and a third domain selected from the group consisting of a detectable moiety, a capture reagent, and a drug binding domain, wherein the linker links the first domain and the third domain. In some instances, the third domain is a detectable moiety, and the detectable moiety is selected from the group consisting of a radioactive isotope, a magnetic compound, an x-ray absorber, a fluorescent molecule, a chemical compound, and a biological tag.

In some cases, the third domain is a capture reagent and is selected from the group consisting of a polyhistidine tag, biotin, chitin binding protein (CBP), maltose binding protein (MBP), glutathione-S-transferase (GST), CYD (covalent yet dissociable NorpD peptide), Strep II, FLAG, and HPC (heavy chain of protein C) peptide tags. In some instances the third domain is a capture reagent and is an affinity tag or a chromatography tag.

In some embodiments, the third domain is a drug binding domain that binds to a drug or biologic agent. The drug binding domain can be a domain that binds RNA, a growth factor, an immunoglobulin, a chemotherapeutic agent, or a human serum albumin. In some instances, the drug-binding domain is a domain that binds a chemotherapeutic agent. The chemotherapeutic agent can be paclitaxel, docetaxel, nab-paclitaxel, methotrexate, or any combination thereof.

In some cases, the drug binding domain is a domain that binds an immunoglobulin. The immunoglobulin can be an anti-CTLA-4, anti-PD-1, or anti-PD-L1 antibody. In some cases, the immunoglobulin is ipililumab, nivolumab, pembrolizumab, azetolizumab, durvalumab, tremelilumab, or any combination thereof. In some instances, the immunoglobulin binding domain binds to a cognate receptor or tumor associated antigen. The cognate receptor or tumor associated antigen can be selected from the group consisting of EGFR (cetuximab), Her2 (trastuzumab, pertuzumab), CD20 (rituximab), CD3 and CD19 (blinatumumab bi-specific T-cell engager), CEA, CD33, or any combination thereof. In some instances, the immunoglobulin binding domain binds to a conjugated monoclonal antibody/toxin (ado-trastuzumab emtansine).

In some embodiments, the drug binding domain binds to an angiogenesis modulating agent. The angiogenesis modulating agent can be selected from a group of growth factors selected from the group consisting of: vascular endothelial growth factor (VEGF), epidermal growth factor (EGF), hepatocyte growth factor (HGF), platelet derived endothelial cell growth factor (PD-ECGF), platelet derived growth factor (PDGF); insulin-like growth factor (IGF), interleukin-8, growth hormone, angiopoietin, acidic and basic fibroblast growth factors (FGFs), transforming growth factor alpha (TGF-alpha.), an enzyme, an enzymatic inhibitor, and an antibody specific for these growth factors and their receptors.

In some cases, the angiogenesis modulating agent is a monoclonal antibody (mAb). In some instances, the mAb is an anti-vascular endothelial growth factor (VEGF) antibody. The mAb can be selected from the group consisting of: bevacizumab, aflibercept, and rilonacept.

In some embodiments, the drug-binding domain is a domain that binds to small interfering RNA (siRNA). In some cases, the binding domain comprises, consists essentially of, or consists of the amino acid sequence of SEQ ID NO: 45 or SEQ ID NO: 46.

In some embodiments, the drug-binding domain is a domain that binds an anti-viral drug.

In some embodiments, the vimentin-binding peptide is an antibody. In some embodiments, the first domain comprises an antibody, wherein the antibody comprises a vimentin-biding peptide.

In some embodiments, the compounds described herein further comprise a human serum albumin (HSA)-binding domain, comprising, consisting essentially of, or consisting of the amino acid sequence of SEQ ID NO: 47 or SEQ ID NO: 48. The HSA-binding domain can be linked to one or more of the vimentin-binding peptide, a third linker, and the third domain.

In some cases, the compounds described herein bind vimentin with an affinity of at least $10^{-7}$ M. In some instances, the compounds described herein bind vimentin with a $K_d$ of less than $10^{-7}$M. In some cases, the compounds described herein bind vimentin with a $K_d$ of about $10^{-14}$ M.

In some cases, the compound comprises an antibody. In some cases, the first domain comprises an antibody and the antibody comprises the vimentin-binding peptide. In some cases, the first domain comprising a vimentin-binding peptide is an antibody. In some instances, the antibody is an anti-vimentin antibody. In some cases, the antibody is an antibody specific for vimentin on the cell surface (e.g., on CTCs). In some cases, the antibody has a therapeutic effect on the CTCs. In some instances, the first domain comprising a vimentin-binding peptide is an antibody, and is used for the capture, detection, targeting, and/or treatment of CTCs.

In some embodiments, the compounds described herein further comprise: a fourth domain that comprises, consists essentially of, or consists of an exposed collagenous (XC) protein binding peptide; and a fifth domain that comprises a second linker, wherein the XC protein binding peptide and the vimentin-binding peptide are connected via the second linker, thereby forming a dual-binding peptide, and the third domain is connected to the dual-binding peptide via the first linker. In some cases, the exposed collagenous (XC) protein binding peptide is a polypeptide derived from a von Willebrand factor collagen binding domain or a conservative variation thereof that retains collagen binding activity. In some instances, the XC protein binding peptide comprises, consists essentially of, or consists of the amino acid sequence of SEQ ID NO: 22, SEQ ID NO: 23, or SEQ ID NO: 24. The XC protein binding peptide can bind to XC proteins present in solid tumors or CTCs. In some cases, the domains are connected by linkers wherein the linkers optimize spacing, flexibility, and/or orientation of the domains.

In some embodiments of all aspects, the first linker comprises, consists essentially of, or consists of the amino acid sequence of any one of SEQ ID NO: 25-44. In some embodiments of all aspects, the second linker comprises, consists essentially of, or consists of the amino acid sequence of any one of SEQ ID NO: 25-44. The linkers described herein can comprise, consist essentially of, or consist of the amino acid sequence of any one of SEQ ID NOs: 25-44 or an Ahx, wherein the linker connects two domains of the compound.

In another aspect, the present disclosure provides for a compound that comprises, consists essentially of, or consists of an amino acid sequence selected from the group consisting of:

```
                                      (SEQ ID NO: 1)
acetyl-VNTANSTGGSGK(FITC)-amide;

(SEQ ID NO: 2)
acetyl-VNTANSTGGSGGVNTANSTGGSGK(FITC)-amide;

(SEQ ID NO: 3)
acetyl-VNTANSTGGSGK(Biotin)-amide;

(SEQ ID NO: 4)
acetyl-SAHGTSTGVPWPGGSGK(FITC)-amide;

(SEQ ID NO: 5)
acetyl-SAHGTSTGVPWPGGSGK(Biotin)-amide;

(SEQ ID NO: 6)
Biotin-Ahx)-SAHGTSTGVPWPGGS-amide;

(SEQ ID NO: 7)
acetyl-VNTANSTGGSGARRGVRVAWREPGRMELNMPHGGSGK(FITC)-
amide;

(SEQ ID NO: 8)
acetyl-VNTANSTGGSGARRGVRVAWREPGRMELNMPHGGSGK
(Biotin)-amide;

(SEQ ID NO: 9)
acetyl-STRSVSSSSYRRMFGGPGTASK(FITC)-amide;

(SEQ ID NO: 10)
acetyl-STRSVSSSSYRRMFGGPGTASK(Biotin)-amide;

(SEQ ID NO: 11)
acetyl-KMALDIEIATYRKLLEGEESRISGSGK(FITC)-amide;

(SEQ ID NO: 12)
acetyl-KMALDIEIATYRKLLEGEESRISGSGK(Biotin)-amide;

(SEQ ID NO: 13)
acetyl-RRGVRVAWREPGRMELNMPHGGSGK(Biotin)-amide;
```

-continued acetyl-KVRFLEQQNKILLAELEQLKGQGK(FITC)-amide; (SEQ ID NO: 14)

acetyl-KVRFLEQQNKILLAELEQLKGQGK(Biotin); (SEQ ID NO: 15)

acetyl-RPKRNDGVVVPRLLDITLRAYDNRKSGK(FITC)-amide; (SEQ ID NO: 16)

acetyl-RPKRNDGVVVPRLLDITLRAYDNRKSGK(Biotin)-amide; (SEQ ID NO: 53)

acetyl-TRKRIRIQRGPGRAFVTIGGK(FITC)-amide; (SEQ ID NO: 17)

acetyl-TRKRIRIQRGPGRAFVTIGGK(Biotin)-amide; (SEQ ID NO: 54)

acetyl-TRKSIHIGPGRAFYTTGGK(FITC)-amide; (SEQ ID NO: 18)

acetyl-TRKSIHIGPGRAFYTTGGK(Biotin)-amide; (SEQ ID NO: 55)

acetyl-RRGVHVGWREPSFMALSMPHGGSGK(FITC)-amide; (SEQ ID NO: 19)

acetyl-RRGVRVAWREPGRMELNMPHGGSGK(FITC)-amide; (SEQ ID NO: 20)

acetyl-RRGVRVAWREPGRMELNMPHGGSGK(Biotin)-amide; (SEQ ID NO: 21)

(FITC-Ahx)AGKKPRVTVTNVFLYNRPLNSTE-free acid; (SEQ ID NO: 49)

(Biotin-Ahx)AGKKPRVTVTNVFLYNRPLNSTE-free acid; (SEQ ID NO: 50)

(FITC-Ahx)AGKKPSVTVTNVFLYNRPLNSTE-free acid; and (SEQ ID NO: 51)

(Biotin-Ahx)AGKKPSVTVTNVFLYNRPLNSTE-free acid. (SEQ ID NO: 52)

In any of the peptides described herein, the N-terminus may be an acetyl-group or an amine group. In any of the peptides described herein, the C-terminus may be a free acid (e.g., a carboxyl group) or an amide group.

In some cases, Ahx is aminohexanoic acid.

In some embodiments, one (e.g., 1, 2, 3, 4, 5, 6, 7, 8, 9, or 10) or more residues in the sequences of the compounds described herein may be modified, wherein the modified compound has increased affinity to vimentin as compared to an unmodified compound. A modification includes amino acid substitutions, deletions, and/or insertions. In some cases, a modification is the modification of a single amino acid. In another case, the amino acid modification is the modification of multiple (e.g., more than one) amino acids. In some cases a modification is a post-translational modification (e.g., glycosylation, sialylation). In some embodiments, the compound is acetylated. In some cases, the compound is PEGylated.

In another aspect, the present disclosure provides for a pharmaceutical composition comprising one or more of the compounds described herein and a pharmaceutically acceptable carrier.

In another aspect, the present disclosure provides for a method of detecting CTCs in a sample, the method comprising: contacting the sample with a compound, wherein the compound comprises, consists essentially of, or consists of: (i) a first domain comprising a vimentin-binding peptide; (ii) a second domain comprising a linker; and (iii) a third domain comprising a detectable moiety; and detecting the compound, to thereby detect CTCs in the sample. The detectable moiety can be a radioactive isotope, a magnetic compound, an x-ray absorber, a fluorescent molecule, a chemical compound, or a biological tag; and wherein detecting the compound comprises detecting the radioactivity, the magnetism, the x-ray absorption, the fluorescence, the chemical, or the biological tag, respectively. In some cases, the compound is localized to the CTCs and detecting the compound comprises detecting the localization of the compound to the CTCs.

In another aspect, the present disclosure provides for a method of detecting cancer in a sample, the method comprising: contacting the sample with a compound, wherein the compound comprises, consists essentially of, or consists of: a first domain comprising a vimentin-binding peptide; a second domain comprising a linker; and a third domain comprising a detectable moiety; and detecting the compound, thereby detecting cancer in the sample. In some instances, the compound binds to vimentin on cancer cells or CTCs and wherein detecting the compound comprises detecting the compound bound to vimentin on the cancer cells or on the CTCs.

In another aspect, the present disclosure provides for a method of detecting a tumor in a sample, the method comprising, consisting essentially of, or consisting of: contacting the sample with a compound, wherein the compound comprises: a first domain comprising a vimentin-binding peptide; a second domain comprising a linker; and a third domain comprising a detectable moiety; and detecting the compound and thereby detecting a tumor in the sample. In some cases, the compound binds to tumor cells and detecting the compound includes detecting the compound bound to tumor cells.

In another aspect, the present disclosure provides for a method of detecting metastatic cancer in a subject, the method comprising, consisting essentially of, or consisting of: contacting a sample from the subject with a compound, wherein the compound comprises: a first domain comprising a vimentin-binding peptide; a second domain comprising a linker; and a third domain comprising a detectable moiety; and detecting the compound in the sample, thereby detecting metastatic cancer in the subject. In some cases, the subject has been diagnosed as having a tumor.

In another aspect, the present disclosure provides for a method of diagnosing cancer in a subject, the method comprising, consisting essentially of, or consisting of: contacting a sample with a compound, wherein the compound comprises: a first domain comprising a vimentin-binding peptide; a second domain comprising a linker; and a third domain comprising a detectable moiety; detecting the compound in the sample; and diagnosing the subject as having cancer when the levels of the compound in the sample are increased when compared to a reference sample. In some cases, the method of diagnosing is an in vitro method of diagnosing.

In another aspect, the present disclosure provides for a method of determining the stage of a cancer, the method comprising, consisting essentially of, or consisting of: contacting a sample with a compound, wherein the compound comprises: a first domain comprising a vimentin-binding peptide; a second domain comprising a linker; and a third domain comprising a detectable moiety; detecting the compound in the sample; comparing the levels of the compound to those of a reference sample; and determining the stage of the cancer based on the comparison to the reference sample.

In another aspect, the present disclosure provides for a method of determining the efficacy of a cancer treatment, the method comprising, consisting essentially of, or consisting of: detecting levels of CTCs in a first sample taken from a subject before administering the cancer treatment, wherein detecting comprises contacting the first sample with a compound and detecting the compound, wherein the compound comprises, consists essentially of, or consists of: (i) a first domain comprising a vimentin-binding peptide; (ii) a second domain comprising a linker; and (iii) a third domain comprising a detectable moiety; detecting levels of CTCs in a second sample taken from the subject after administering the cancer treatment, wherein detecting comprises contacting the second sample with the compound and detecting the compound; and determining the efficacy of the cancer treatment by comparison of the levels of CTCs in the first and second samples.

In some embodiments, the compound further comprises: a fourth domain that comprises an exposed collagenous (XC) protein binding peptide; and a fifth domain that comprises a second linker, wherein the XC protein binding peptide and the vimentin-binding peptide are connected via the second linker, thereby forming a dual-binding peptide, and the third domain is connected to the dual-binding peptide via the first linker. In some embodiments, the sample is a blood sample or blood biopsy. In some embodiments, contacting the sample with the compound is performed ex vivo, in vivo or in vitro.

In another aspect, the present disclosure provides for a method of treating CTCs in a subject, the method comprising, consisting essentially of, or consisting of administering to a subject in need of such a treatment any one or more of the compounds described herein in an amount sufficient to treat the CTCs.

In another aspect, the present disclosure provides for a method of treating a tumor in a subject, the method comprising, consisting essentially of, or consisting of administering to a subject in need of such a treatment any one or more of the compounds described herein in an amount sufficient to treat the tumor.

In another aspect, the present disclosure provides for a method of treating cancer in a subject, the method comprising, consisting essentially of, or consisting of administering to a subject in need of such a treatment any one or more of the compounds described herein in an amount sufficient to treat the cancer.

In another aspect, the present disclosure provides for a method of treating CTCs in a subject, the method comprising, consisting essentially of, or consisting of administering to a subject in need of such a treatment one or more of the pharmaceutical compositions described herein in an amount sufficient to treat the CTCs.

In another aspect, the present disclosure provides for a method of treating a tumor in a subject, the method comprising, consisting essentially of, or consisting of administering to a subject in need of such a treatment one or more of the pharmaceutical compositions described herein in an amount sufficient to treat the tumor.

In another aspect, the present disclosure provides for a method of treating cancer in a subject, the method comprising, consisting essentially of, or consisting of administering to a subject in need of such a treatment one or more of the pharmaceutical compositions described herein in an amount sufficient to treat the cancer.

In some embodiments, the tumor is a primary or metastatic cancer selected from the group consisting of: colorectal cancer, breast cancer, brain cancer, non-small cell lung cancer, gastrointestinal cancer, bladder cancer, ovary cancer, uterine cancer, pancreas cancer, lung cancer, pancreatic cancer, prostate cancer, sarcoma, glioma, carcinoma, and melanoma. In some cases, the cancer is a primary or metastatic cancer selected from the group consisting of: colorectal cancer, breast cancer, brain cancer, non-small cell lung cancer, gastrointestinal cancer, bladder cancer, ovary cancer, uterine cancer, pancreas cancer, lung cancer, pancreatic cancer, prostate cancer, sarcoma, glioma, carcinoma, and melanoma.

In some instances, the compound is administered before, after, or concurrently with an additional therapeutic agent. In some instances, the pharmaceutical composition is administered before, after, or concurrently with an additional therapeutic agent.

In another aspect, the present disclosure provides for a method of diagnosing a viral infection in a sample, the method comprising, consisting essentially of, or consisting of: contacting a sample with a compound, wherein the compound comprises, consists essentially of, or consists of: a first domain comprising a vimentin-binding peptide; a second domain comprising a linker; and a third domain comprising a detectable moiety; detecting the compound in the sample; and diagnosing the sample as having a viral infection when the level of compound in the sample is increased as compared to a reference level.

In another aspect, the present disclosure provides for a method of detecting viral particles in a sample, the method comprising, consisting essentially of, or consisting of: contacting a sample with a compound, wherein the compound comprises: a first domain comprising a vimentin-binding peptide; a second domain comprising a linker; and a third domain comprising a detectable moiety; detecting the compound in the sample; and detecting viral particles in the sample when the level of compound in the sample is increased when compared to the level of compound in a reference sample.

In another aspect, the present disclosure provides for a method of treating a viral infection in a subject, the method comprising, consisting essentially of, or consisting of: administering to a subject in need of such treatment the compound, wherein the drug-binding domain is a domain that binds an anti-viral drug, in an amount sufficient to treat the viral infection. In some cases, the compound is administered before, after, or concurrently with an additional therapeutic agent.

In another aspect, the present disclosure provides for a method of isolating CTCs from a sample, the method comprising, consisting essentially of, or consisting of: contacting the sample with a compound, wherein the compound comprises: (i) a first domain comprising a vimentin-binding peptide; (ii) a second domain comprising a linker; and (iii) a third domain comprising a capture reagent, thereby forming a mixture; contacting the mixture with an immobilizing agent, wherein the immobilizing agent binds to the capture reagent; thereby isolating the CTCs from the sample. In some cases, the immobilizing agent is immobilized on a solid support. In some instances, the immobilizing agent is immobilized after binding to the capture reagent. In some cases, the sample is a blood biopsy.

In some instances, the methods further comprise removing the CD45+ cells from the sample before contacting the sample with the compound. In some instances, the methods further comprise performing size chromatography on the sample prior to contacting the sample with the compound, such that the sample is enriched for the CTCs.

In some cases, the method further comprises removing the immobilizing agent from the sample, thereby removing CTCs from the sample. The immobilizing agent can comprise, consist essentially of, or consist of a magnetic bead.

In some instances, the method further comprises, consists essentially of, or consists of applying a magnetic force to the mixture; washing the mixture; separating the CTCs from the compound; and removing the magnetic beads. In some cases, the capture reagent comprises, consists essentially of, or consists of biotin and contacting the mixture with an immobilizing agent comprises contacting the mixture to streptavidin or avidin that is bound to a solid surface. In some instances, the method further comprises: washing the mixture on the compound on the streptavidin or avidin; and eluting the CTCs from the compound. In some cases, the method further comprises characterizing the CTCs, wherein characterizing comprises performing one or more of genetic analysis, proteomic analysis, metabolomics and transcriptomics.

In another aspect, the present disclosure provides for a resin, comprising a compound, wherein the compound comprises, consists essentially of, or consists of a first domain comprising a vimentin-binding peptide, and the compound is immobilized on the resin. In some instances, the resin further includes: a second domain comprising a linker; wherein the compound is immobilized on the resin via the linker. In some cases, the compound further comprises: a third domain that comprises an exposed collagenous (XC) protein binding peptide; and a fourth domain that comprises a second linker, wherein the XC protein binding peptide and the vimentin-binding peptide are connected via the second linker, thereby forming a dual-binding peptide, and the dual-binding peptide is immobilized on the resin via the first linker.

In another aspect, the present disclosure provides for a chromatography column comprising, consisting essentially of, or consisting of the resin described herein.

In another aspect, the present disclosure provides for a solid support comprising, consisting essentially of, or consisting of the resin described herein.

In another aspect, the present disclosure provides for a solid support having a plurality of compounds comprising a vimentin-binding peptide immobilized thereon. In some cases, the compounds further comprise: a second domain comprising a linker; wherein the compound is immobilized on the solid support via the linker. In some cases, the compounds further comprise: a third domain that comprises an exposed collagenous (XC) protein binding peptide; and a fourth domain that comprises a second linker, wherein the XC protein binding peptide and the vimentin binding peptide are connected via the second linker, thereby forming a dual-binding peptide, and the dual-binding peptide is immobilized on the solid support via the first linker.

In another aspect, the present disclosure provides for a method of removing CTCs from a subject's blood, the method comprising, consisting essentially of, or consisting of: contacting the subject's blood to a solid support comprising one of the following immobilized thereon: (a) a vimentin-binding peptide; or (b) a compound, wherein the compound comprises a vimentin-binding peptide linked to a capture reagent, and wherein the capture reagent is immobilized on the solid support; to thereby remove CTCs from the subject's blood. In some instances, the subject has been diagnosed as having cancer.

In some embodiments, the method further comprises: administering a drug or biologic agent to the subject. In some cases, the drug or biologic agent is administered before, after, or concurrently with removing the CTCs. The drug or biologic can be selected from the group consisting of an RNA, siRNA a growth factor, an immunoglobulin, a chemotherapeutic agent, human serum albumin, and an angiogenesis modulating agent. The drug or biologic can also be any of the compounds described herein.

In some cases, the solid support is configured for insertion into an apheresis device. In some instances, prior to contacting, the subject's blood is withdrawn from the subject, and wherein after contacting, the subject's blood is infused back into the subject.

In another aspect, the present disclosure provides for a method of screening for agents that bind to vimentin, the method comprising: providing a test agent; contacting the test agent with any one or more of the compounds described herein; and identifying the test agent that binds to the compound, thereby identifying an agent that binds to vimentin.

As used herein, the term "aptamer" is art-known and refers to an oligonucleotide or polypeptide that binds to a specific target molecule with high affinity and specificity.

The term "collagen-binding domain" is known in the art and refers to any polypeptide, or portion thereof, that can bind collagen, e.g., the collagenous proteins that are newly expressed and/or exposed in injured tissues and invasive cancers, as well as collagenous affinity matrices prepared in vitro. Several collagen-binding domains are known in the art (Cruz M A, et al., J. Biol. Chem., 270:10822-10827, 1995; Hoylaerts, M. F., et al., Biochem. J., 324:185-191, 1997; Lankhof, H., et al., Thrombos Haemostas, 75:950-958, 1996, which are incorporated herein in their entirety).

The term "vimentin-binding domain" is known in the art and refers to any polypeptide, antibody, or portion thereof, that can bind vimentin as well as vimentin affinity matrices prepared in vitro.

The term "human serum albumin-binding domain" or "HSA-binding domain" refers to a structure that comprises a thiol-reactive maleimide group or a polypeptide, or portion thereof, that can bind human serum albumin.

The term "treatment" refers to the administration of one or more pharmaceutical agents to a subject or the performance of a medical procedure on the body of a subject. The term treatment also includes an adjustment (e.g., increase or decrease) in the dose or frequency of one or more pharmaceutical agents that a subject can be taking, the administration of one or more new pharmaceutical agents to the subject, or the removal of one or more pharmaceutical agents from the subject's treatment plan.

The term "subject" is used throughout the specification to describe an animal, human or non-human, rodent or non-rodent, to whom treatment according to the methods of the present invention is provided. Veterinary and non-veterinary applications are contemplated. The term includes but is not limited to birds, reptiles, amphibians, and mammals, e.g., humans, other primates, pigs, rodents such as mice and rats, rabbits, guinea pigs, hamsters, cows, horses, cats, dogs, sheep and goats. Preferred subjects are humans, farm animals, and domestic pets such as cats and dogs.

An "effective amount" is an amount sufficient to effect beneficial or desired results. For example, a therapeutically effective amount is one that achieves the desired therapeutic effect. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments. Effective amounts in the present context include, for example, amounts effective to reduce or shrink a tumor, reduce the incidence of metastasis in a cancer subject, reduce the number of circulating cancer cells in the subject and/or reduce the number of viruses in the subject.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIGS. 1A, 1B, and 1C are schematic diagrams of the pericellular matrix or glycocalyx of circulating tumor cells (CTCs) and specific cell-surface proteins. FIG. 1A is a cartoon diagram of the CTC cell surface proteins including collagen(s) and vimentin filaments. FIG. 1B is a schematic demonstrating the multifunctional domains of the exposed collagen binding compounds. FIG. 1C is a schematic demonstrating the multifunctional domains of the vimentin-binding compounds.

FIG. 2 is a diagram of vimentin structure, as a monomer, a dimmer, and a tetramer.

DETAILED DESCRIPTION

Figure 3:
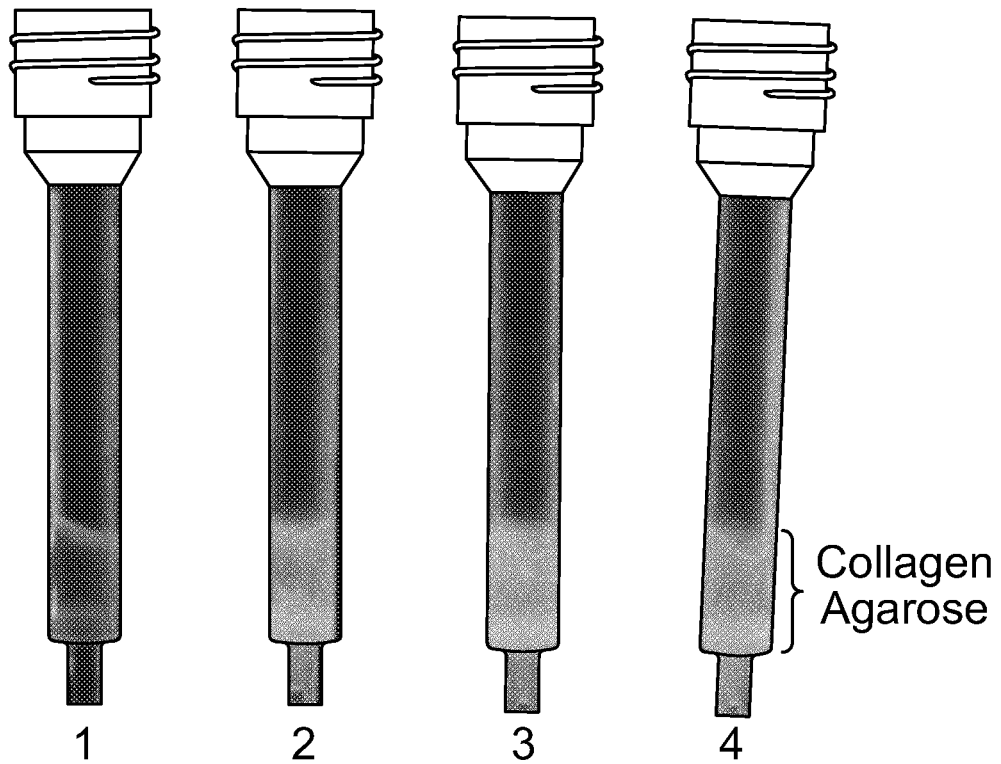
FIG. 3 is a schematic and a photograph of a collagen agarose binding assay. Apt #1 is an aptamer consisting of SEQ ID NO: 1; Apt #7 is an aptamer consisting of SEQ ID NO: 7; Apt #19 is an aptamer consisting of SEQ ID NO: 19; and Apt #20 is an aptamer consisting of SEQ ID NO: 20. CBD=collagen-binding domain; CBD1=bovine vWF sequence comprising SEQ ID NO: 22; CBD2=human vWF sequence comprising SEQ ID NO: 23.

The present disclosure is based, at least in part, on the development of new compounds that include polypeptide binding peptides that are selective for abnormal cell surface vimentin protein (XV, exposed vimentin) embedded within the pericellular matrix of CTCs. These compounds may be used clinically for differential diagnosis, subject monitoring, cancer characterization, or targeted cancer therapy. In addition to physically targeting one or more of these pericellular matrix proteins, the polypeptide binding peptides can be physically coupled, through a linker, to an additional functional domain that can be, e.g., a CTC reporter molecule or detectable moiety (e.g., FITC), capture reagent (e.g., Biotin), a therapeutic bioactive agent (e.g., methotrexate), a drug binding domain (e.g., an immunoglobulin binding domain), or any combination thereof. In some instances, more than one functional domain can be linked to the polypeptide binding peptide. The polypeptide binding peptides can additionally be linked to binding peptides that are selective for abnormal cell surface collagens (XC, exposed collagens) that are embedded within the pericellular matrix of CTCs. In general, these compounds include three or more domains: (1) a vimentin-binding peptide; (2) a linker; and (3) at least one functional moiety.

The vimentin-binding peptides of the present disclosure provide for a selective and efficient targeting of cancer cells expressing exposed vimentin proteins. This intermediate filament protein, vimentin, is trans-located onto the pericellular surfaces in many different cancer cells, and thus the different cells can be selectively targeted. The vimentin-binding compounds of this disclosure comprise a vimentin-binding domain that is selective for the exposed cell surface vimentin protein (monomer) and/or the assemblage of exposed vimentin (XV) filaments that are arrayed on the cell surface of CTCs. In some instances, the compound is designed to include both the vimentin-binding peptide and a collagen binding peptide, for even broader cancer cell targeting.

These compounds provide new and powerful clinical tools (i.e. diagnostic and therapeutic reagents) for the characterization and/or capture of both mesodermal CTCs and EMT-positive CTCs, for elucidating the nature of metastatic progression in greater detail, for monitoring subject responses to cancer therapies, and/or as a selective and precisely-targeted drug delivery platform.

Compounds that Selectively Target the Cancer Microenvironment

The fundamental "hallmarks of cancer"—sustained proliferative signaling, evading growth suppressors, resisting cell death, activating programs of invasiveness, metastasis, and angiogenesis—can be viewed collectively as a unifying series of acquired capabilities that govern the transformation of normal cells into high-grade malignant cancers (Hanahan and Weinberg, Hallmarks of Cancer: the next generation. Cell, 2011, 144:646-674). Paramount among these acquired malignant cell characteristics are permissive and progressive interactions with the tumor microenvironment (Pietrasa and Ostmanb, Hallmarks of cancer: interactions with the tumor stroma. Exp. Cell Res., 2010, 313:1324-1331): including the abundance of collagenous proteins within the extracellular matrix (Fang et al., Collagen as a double-edged sword in tumor progression. Tumor Biol., 2014, 35:2871-2882); the hijacking of collagen receptors (i.e., integrin and discordin domain receptors) by tumor cells to disrupt normal cell-matrix communications and initiate pro-migratory and pro-invasive programs (Mierke et al., Integrin a-5b-1 facilitates cancer cell invasion through enhanced contractile forces. J. Cell Science, 2010, 124:369-383; and Valiathan et al., Discoidin domain receptor tyrosine kinases: new players in cancer progression. Cancer Metastasis Rev., 2012, DOI 10.1007/s10555-012-9346-z); and the tendency of epithelioid cancer cells to undergo an epithelial-to-mesenchymal transition (Thiery, Epithelial-mesenchymal transitions in tumor progression. Nature Reviews, 2002, 2:442-454; and Talbot et al., Epithelial-mesenchymal transition, the tumor microenvironment, and metastatic behavior of epithelial malignancies, Int J Biochem Mol Biol. 2012, 3:117-136), which leads to an increase in motile "fibroid" morphology, invasiveness, resistance to apoptosis, and an increase in extracellular matrix components. During this progression of cancer cells to more-aggressive, treatment-resistant phenotypes, the cells abnormally express the cell surface vimentin protein, a characteristically mesenchymal protein (Satelli and Li, Vimentin, an overview and its potential as a molecular target for cancer therapy. Cell Mol Life Sci. 2011, 68: 3033-3046; and Satelli et al., Epithelial-mesenchymal transitioned circulating tumor cells capture for detecting tumor progression. Clin Cancer Res, 2014, 21:1-8), and collagen adhesion matrix (CAM) (Lu et al., Isolation of circulating epithelial and tumor progenitor cells with an invasive phenotype from breast cancer patients, Int J Cancer. 2010, 126: 669-683). Thus, the abnormal exposure of collagenous proteins and vimentin is a characteristic histopathologic property of many cancers and neoplastic lesions.

The onset of tumor metastasis, which contributes to the vast majority of cancer related deaths, involves the dissemination of an increasingly heterogeneous population of primary tumor cells and cancer stem cells that are epigenetically undergoing the EMT (Chaffer and Weinberg, A perspective on cancer cell metastasis. Science, 2011, 331: 1559-1564; and Patel and Chen, Cancer stem cells, tumor dormancy, and metastasis. Frontiers in Endocrin. 2012, 3: 1-5), thereby generating more mesenchymal-like CTCs that can escape from EpCAM-based detection methods (Gorges et al. Circulating tumour cells escape from EpCAM based detection due to epithelial-to-mesenchymal transition. BMC Cancer 2012, 12:178-191; Heerboth et al., EMT and tumor metastasis. Clinical and Translational Medicine, 2015, 4:1-13; and Schneck et al., EpCAM-Independent Enrichment of Circulating Tumor Cells in Metastatic Breast Cancer. PLOS ONE DOI:10.1371/journal.pone.0144535 2015, Dec.: 1-23). Cells undergoing the EMT lose epithelial cell-to-cell contacts and tight junctions, in favor of a spindle shaped morphology with enhanced motility. This transition is correlated with a molecular-genetic switch in cellular intermediate filament proteins from the keratins (epithelial cells) to vimentin (characteristic of mesenchymal cells) (Satelli and Li, Vimentin, an overview and its potential as a molecular target for cancer therapy. Cell Mol Life Sci. 2011, 68: 3033-3046; Satelli et al., Epithelial-mesenchymal transitioned circulating tumor cells capture for detecting tumor progression. Clin Cancer Res, 2014, 21:1-8; and Dave et al., Epithelial-mesenchymal transition, cancer stem cells and treatment resistance. Breast Cancer Res., 2012, 14:202-207). Thus, the vimentin-binding peptides of the present disclosure can be used for molecular targeting of vimentin filaments displayed on the surface of tumor cells (exposed-vimentin 'XV'). Additionally, the process of tumor invasion, metastasis, angiogenesis, and reactive stroma formation disrupts normal tissue histology and leads to pathologic exposure of collagenous proteins (XC–) within the tumor microenvironment. Thus, the abnormal exposure of collagenous proteins is another characteristic histopathologic property of all neoplastic lesions. The vimentin-binding or vimentin/collagen-dual-binding peptides described herein allows for efficient diagnosis and the targeting of therapeutic agents to pathological areas and facilitates the efficient isolation and characterization CTCs.

"Pathotropic (disease-seeking) Targeting" of drugs to cancerous tissues utilizes the pathology of the tumor itself (exposed-protein expression) as the biochemical target, rather than the unique, varied, rapidly evolving cancer cells per se. By targeting a common histopathologic property of primary tumors and metastatic lesions, the drug delivery systems described herein can (i) bind and carry a well-characterized (e.g., FDA-approved) therapeutic drug, upon simple mixing, and (ii) seek-out and accumulate on the diseased/cancerous cells upon intravenous infusion. The advent of Pathotropic Targeting ushered the field of genetic medicine into the clinic (Waehler et al., Nature Reviews Genetics 8:573-587, 2007). Further advancement of the field of targeted antitumor therapy was made with the development of Rexin-G (Hall et al., Hum Gene Ther 11:983-993, 2000; Gordon et al., Cancer Res. 60:3343-3347, 2000; Hall et al., Intl J Mol Med 6:635-643, 2000)—a nanoparticle gene delivery system which incorporates a physiological surveillance function inherent in the primary structure of von Willebrand Factor-to enable a specific gain-of-function that is highly selective for the pathologic stroma that is characteristic of neoplastic lesions (Gordon et al., Cancer Res. 60:3343-3347, 2000). Indeed, the clinical administration of this tumor-targeted Rexin-G vector has been shown to accumulate in primary and metastatic lesions, resulting in enhanced cytotoxic gene delivery, and thus enhanced clinical efficacy (Gordon et al., Expert Opin Biol Ther 10:819-832, 2010; Gordon et al., Int'l J Oncol 36:1341-1353, 2010; Chawla et al., Mol Ther 2009; 17(9):1651-7; Chawla et al., Mol Ther 2010; 18:435-441).

Provided herein are novel multifunctional compounds that target pathological areas, specifically CTCs. The compounds were molecularly engineered to contain at least three domains: (i) a first domain comprising a vimentin-binding peptide, (ii) a second domain comprising a linker or a spacer, and (iii) at least a third domain for therapeutic, diagnostic or isolation purposes (e.g., a detectable moiety, a capture reagent, a bioactive drug, or a drug binding domain). In some cases, the first domain comprises a collagen-binding peptide. The compound can also include (iv) a fourth domain that comprises an exposed collagenous (XC) protein binding peptide and/or (v) a fifth domain comprising a second linker. The linkers can be used to reduce steric hindrance between the domains and link the separate domains within the compound. These compounds can include sequences or modifications to improve the functionality, pharmacokinetics, stability, and/or pharmacodynamics of the targeted compounds. These compounds allow for the targeted delivery of, inter alia, molecular markers, capture moieties, and therapeutic agents to cancerous cells such as CTCs.

The compounds described herein include a vimentin-binding domain. The monomer protein of vimentin can self-assemble into dimers, tetramers, filaments etc., in the pericellular matrix or glycocalyx of CTCs and vimentin targeting and binding domains described herein may target each of these structures. In some embodiments, the vimentin-binding domain is derived from the sequence of the vimentin protein itself, based on the high affinities of intermediate filament self-assembly. In some constructs, the vimentin-binding domain is a derivative or variation of a vimentin peptide sequence. The vimentin-binding domains described herein may provide a high-affinity interaction with exposed vimentin protein.

In other vimentin-binding constructs, the sequences are derived from interactions with specific viral proteins. The vimentin-binding peptides described herein may be used for targeted delivery to viruses. Viruses exploit cellular machinery for various events including viral entry into a cell, and the major cellular contributors in this process are cytoskeletal components, such as microfilaments, microtubules, and vimentin. For example, vimentin associates directly with outer capsid proteins of viruses, including but not limited to the outer capsid protein VP2 of Bluetongue Virus and the gp120 envelope protein of HIV-1 (Sirpada and Dayaraj, Cell Health and Cytoskeleton, 23 Mar. 2010. Vol 2010:2 Pgs 1-7; Bhattacharya et al., Virol J., (2007) 4 (1). p. 7; Thomas et al, Viral Immunol. 1996:9(2):73-87; and Jiang et al., Nature Structural & Molecular Biology. 17, 955-961 (2010)). These virus-to-vimentin interactions were adaptively engineered into novel vimentin-binding peptides, as described herein, e.g., SEQ ID NOs: 16-18. Vimentin also associates directly with an adhesive surface glycoprotein (a trans-sialidase), which is expressed by the parasite, *Trypanosoma cruzi*, that is responsible for Chagas disease (Magdesian et al., The Journal of Biological Chemistry, 7 Mar. 2001; and Teixeira et al., PLOS Neglected Tropical Diseases, 23 Sep. 2015). This protozoan-to-vimentin interaction was adaptively engineered into novel vimentin-binding peptides, as described herein, e.g., SEQ ID NOs: 49-52.

The vimentin-binding peptides of this disclosure may also target viruses. The virus binding compounds may comprise the drug binding domain that can bind an anti-viral drug. This can provide for efficient delivery of an anti-viral drug to the virus, e.g., the capsid or envelope of a specific virus.

The compounds described herein can have a collagen-binding domain (collagen-targeting peptide). This collagen-binding domain can be separate, or in addition to the vimentin-binding peptide. The compounds described herein that include both the vimentin and collagen-binding peptides can include linkers to separate the targeting domains and reduce any steric hindrance of the domains. For example, a compound may include a vimentin-binding peptide connected on the C-terminus by a linker to the N-terminus of a collagen-binding peptide, the C-terminus of the collagen-binding peptide is then connected by a linker to the third domain. In another example, a compound may include a collagen binding peptide connected on the C-terminus by a linker to the N-terminus of a vimentin-binding peptide, which is then connected by a linker to the third domain. In some embodiments, the vimentin- and collagen-binding domains are directly connected to each other without a linker. In some embodiments, the collagen-binding domain is derived from a collagen-binding domain of von Willebrand factor, which is involved in the recognition of exposed vascular collagen (Takagi, J., et al., Biochemistry 32:8530-4, 1992; Tuan, T. L., et al., Conn. Tiss. Res. 34:1-9, 1996; Gordon, E. M., et al., Hum. Gene Ther. 8:1385-1394; U.S. Pat. No. 6,387,663, all herein incorporated by reference). von Willebrand factor was initially identified as a hemostatic factor in studies of inherited hemophilias (Wagner, Ann. Rev. Cell. Biol. 6:217, 1990), and has been shown to perform a vital surveillance function by targeting platelet aggregates to injured/diseased tissues and vascular lesions (Ginsburg and Bowie, Blood 79:2507-2519, 1992). The collagen binding peptide can comprise, for example, the sequence WREPSFMALS (SEQ ID NO: 22), WREPGRMELN (SEQ ID NO: 23), and/or CGSGGSGGSGARRGVHVGWREPGRMELNMPHG(D-Gln)(D-Pro)(D-Thr)-amide (SEQ ID NO: 24). Other collagen binding domains and constructs are known in the art, for example, see United States Patent Application Publication WO 2016/054107, which is incorporated herein in its entirety.

The compounds can be engineered and used, e.g., for imaging and/or tracking primary and/or metastatic tumors in a subject. For example, the compounds can include a detectable moiety, such as a radioactive isotope, a magnetic compound, an x-ray absorber, a fluorescent molecule, a chemical compound, and/or a biological tag. After administering the labeled compound to a subject, the compounds are targeted to the primary tumors, metastatic tumors, and CTCs in the subject through its vimentin binding domain. Tumors and tumor cells can then be detected using computed tomography, radiography, magnetic resonance imaging, laser scanning microscopy, immunohistochemistry, fluorescent microscopy, Raman spectroscopy, optical coherence tomography (OCT), detection of radiation (e.g., x-ray) scattering or absorption, ultrasound, and/or isotope detection. Practitioners will appreciate that determining the dose to be administered to the subject for imaging or tracking is within the skill of the practitioner and will depend upon the type and location of the tumor(s) in the subject, the type of detectable moiety to be used, and the type of imaging to be performed.

The compounds can include a capture reagent, e.g., a physical capture reagent, for isolating or removing the CTCs. The capture reagent can be, e.g., biotin, a polyhistidine tag, chitin binding protein (CBP), maltose binding protein (MBP), glutathione-S-transferase (GST), CYD (covalent yet dissociable NorpD peptide), Strep II, FLAG, and HPC (heavy chain of protein C) peptide tags. The capture reagent can facilitate the immobilizing of the CTC on a solid support which can then be used for, e.g., imaging, isolating, removing, destroying, or characterizing the CTCs. The capture reagent provides for the selection of the CTCs out of a solution or sample, purifying CTCs, isolating CTCs, enriching a sample for CTCs, removing or destroying cancerous cells, tumor cells, or CTCs. The capture reagent can itself be an immobilized reagent or the capture reagent might bind to an immobilized reagent.

The compounds can include a drug binding domain. The drug-binding properties of these domains are based on high-affinity, non-covalent interactions, which do not substantially alter the chemical composition or the commercial manufacturing of the pharmaceutical agents. In some embodiments the compounds do not comprise the therapeutic agent itself. This facilitates production by chemical synthesis, avoiding the production and purification methodologies required for larger proteins prepared from biologic sources that are associated with a myriad of medical, pharmacological, and regulatory concerns. The chemical structure and pharmaceutical purity of these newly-developed tumor targeting peptides and the compounds that contain them are readily verifiable—by virtue of the synthetic chemistries involved. Furthermore, the chemical composition and commercial manufacture of the bioactive pharmaceutical agents to be delivered by these targeting compounds are not substantially altered due to the non-covalent binding.

In some instances, the drug binding domain of the compound includes human serum albumin (HSA), wherein the HSA can in turn bind a therapeutic agent. For example, the HSA-binding domain of the compounds described herein can have the amino acid sequence of TRSFCTDW-PAHKSCKPL (SEQ ID NO: 47), and/or RQMEDICL-PRWGCLWGD (SEQ ID NO: 48), or variants of these sequences. Albumin, a versatile protein carrier for drug delivery, has been shown to be nontoxic, non-immunogenic, biocompatible, and biodegradable. Albumin-mediated drug delivery systems have gained considerable attention owing to their high binding capacity of various drugs, and the tendency of good tolerance and less side-effects. Albumin was used to fabricate various nanoparticles and targeting vehicles for improving the therapeutic delivery of many drugs (Kratz, J. Controlled Release, 2008, 132:171-83; Kinam Park, J. Controlled. Release, 2012, 157:3; Kwon et al., J. Controlled Release, 2012, 164:108-14). Human serum albumin (HSA) can bind and transport copper (Quinlan et al., Hepatology, 41:1211-1219, 2005), including copper-based radiopharmaceuticals and PET imaging tracers (Lux et al., Theranostics, 5:277-288, 2015). Due to its passive entry into tumors via the enhanced permeability of tumor vasculature and a retention effect caused by increased demand for albumin by tumor cells as a source of energy and amino acids, albumin-based drug delivery systems have been shown to be useful for achieving improved cancer chemotherapy. The delivery of insoluble taxanes, for example, has been improved by the use of lipid-based solvents and albumin as a vehicle. The most popular formulation of albumin-bound paclitaxel (i.e., Abraxane) facilitates the infusion of this biocompatible vehicle, improves the tolerability, and lessens side effects; although enhanced efficacy is generally seen with higher, not lower, drug doses (Miele et al., Int. Journal of Nanomedicine, 2009, 4:91-97). Moreover, the U.S. FDA has made it clear that the passive tumor targeting by albumin does not provide the selectivity required for specific tumor-binding although it may improve the solubility and/or the clinical dosing of drugs (Department of Health & Human Services, NDA #021660 Abraxane® for Injectable Suspension. Reference ID: 3063889).

In some cases, the third domain can be or include a drug or biologic agent itself, e.g., methotrexate. For example, the drug or biological agent may be covalently bound to the linker, or to a side-chain of the linker, e.g., doxorubicin, paclitaxel, camptothecin, cisplatin, and radioisotopes can be bound or linked to the linkers and/or binding-peptides.

Compounds and domains described herein can be modified to include N- and C-terminal modification, e.g., a shielding group on the terminus of the peptide or compound. Non-limiting examples of these N- and C-terminal modifications are the addition of a PEG (poly(ethylene glycol)) moiety or a maleimide group to link covalently with albumin via human serum albumin (HSA) Cys-34. Both of these additions may shield the compound from degradation, increase the stealth of the compound and therefore may improve the circulating half-life of the compounds. The covalent tethering of HSA may serve to resist proteolytic degradation by serum proteases and additionally may reduce filtration of the targeting compound by the kidneys. The addition of a maleimide group would enable site-specific covalent coupling of a peptide domain containing a thiol-reactive group with a free cysteine residue, wherein, for example, the free cysteine residue could be that of the albumin protein or attached to the end of a peptide to allow for site-specific covalent linking. Additional C-terminal modifications include protease-resistant "caps". These caps are D-amino acid substituted "caps" on the terminus of the peptide or compound that may inhibit proteolysis of the aptamers by amino-peptidases and carboxypeptidases present in serum. These D-amino acid substituted "caps" are denoted herein by three letter coded amino acids in the lower case or by "D-" followed by the three letter amino acid code. In some cases, the compound can be acetylated, amidated, and/or PEGylated. Other modifications are known in the art, including, e.g., see Biomatik Peptide Modification List, which is incorporated herein in its entirety.

The compounds described herein can include at least one linker or spacer to reduce the steric hindrances between the other functional domains. Linkers can comprise an amino acid sequence selected from the group consisting of SEQ ID NO: 25-44, e.g., GGSGY (SEQ ID NO: 25); GSAGSAAGSG (SEQ ID NO: 26); GAEAAAKEAAAKAG (SEQ ID NO: 27); GGGG (SEQ ID NO: 28); GGSG (SEQ ID NO: 29); RRGVHVG (SEQ ID NO: 30); (D-Arg)(D-Arg)GVHVG (SEQ ID NO: 31); KGRRGVHVG (SEQ ID NO: 32); GGGGG (SEQ ID NO: 33); GGSGG (SEQ ID NO: 34); SGGSG (SEQ ID NO: 35); GSGSGS (SEQ ID NO: 36); GGSGGSK (SEQ ID NO: 37); GSGGSGSG (SEQ ID NO: 38); GGSGGSGG (SEQ ID NO: 39); GGRRGVHVG (SEQ ID NO: 40); CGSGG (SEQ ID NO: 41); GG (SEQ ID NO: 42); CGRRGVHVG (SEQ ID NO: 43); and/or CARRGVHVG (SEQ ID NO: 44), or any combination thereof. Other linkers are known in the art, e.g., see Priyanka et al., Horn and Sticht, and Chen et al. (Priyanka et al., Protein Science, 2013, Vol 22:153-167; Horn and Sticht, Frontiers in Bioengineering and Biotechnology, November 2015, vol 3, Article 191; and Chen et al., Adv Drug Deliv Rev. 2013 Oct. 15; 65(10):1357-1369), which are incorporated herein in their entirety. The linker can also comprise aminohexanoic acid (Ahx).

Generation of the Tumor-Targeted Compounds

The synthesis or construction of the compounds disclosed herein can be performed by any of the methods known in the art. Peptides can be produced, e.g., by expression of a recombinant nucleic acid encoding the peptide or by chemical synthesis (e.g., by solid-phase synthesis and Fmoc chemistries or other methods well known in the art, including synthesis with an ABI peptide synthesizer; Applied Biosystems, Foster City, Calif.). For example, a peptide can be produced by expression of a nucleic acid encoding the peptide in prokaryotes. These include but are not limited to microorganisms such as bacteria transformed with recombinant bacteriophage DNA, plasmid DNA or cosmid DNA expression vectors encoding a protein of the invention. The constructs can be expressed in *E. coli* in large scale for in vitro assays. Purification from bacteria is simplified when the sequences include tags for one-step purification by nickel-chelate chromatography. The construct can also contain a tag to simplify isolation of the compound. For example, a polyhistidine tag of, e.g., six histidine residues, can be incorporated at the amino terminal end of the fluorescent protein. The polyhistidine tag allows convenient isolation of the protein in a single step by nickel-chelate chromatography. The compounds described herein can also be engineered to contain a cleavage site to aid in protein recovery. Alternatively, the peptides described herein can be expressed directly in a desired host cell for assays in situ.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransfected with DNA sequences encoding the peptides of the invention, and a second foreign DNA molecule encoding a selectable phenotype, such as the herpes simplex thymidine kinase gene. Another useful method includes using a eukaryotic viral vector, such as simian virus 40 (SV40) or bovine papilloma virus, to transiently infect or transform eukaryotic cells and express the peptides. (Eukaryotic Viral Vectors, Cold Spring Harbor Laboratory, Gluzman ed., 1982).

Eukaryotic systems, and preferably mammalian expression systems, allow for proper post-translational modifications of expressed mammalian proteins and peptides to occur. Eukaryotic cells which possess the cellular machinery for proper processing of the primary transcript, glycosylation, phosphorylation, and, advantageously secretion of the gene product should be used as host cells for the expression of fluorescent indicator. Such host cell lines may include but are not limited to CHO, VERO, BHK, HeLa, COS, MDCK, Jurkat, HEK-293, and W138.

For long-term, high-yield production of recombinant proteins, stable expression can be used. Rather than using expression vectors which contain viral origins of replication, host cells can be transformed with the cDNA encoding a peptide of the invention controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci which in turn can be cloned and expanded into cell lines. For example, following the introduction of foreign DNA, engineered cells may be allowed to grow for 1-2 days in an enriched media, and then are switched to a selective media. A number of selection systems may be used, including but not limited to the herpes simplex virus thymidine kinase (Wigler, et al., Cell, 11:223, 1977), hypoxanthine-guanine phosphoribosyltransferase (Szybalska & Szybalski, Proc. Natl. Acad. Sci. USA, 48:2026, 1962), and adenine phosphoribosyltransferase (Lowy, et al., Cell, 22:817, 1980) genes can be employed in tk-, hgprt- or aprt-cells respectively. Also, antimetabolite resistance can be used as the basis of selection for dhfr, which confers resistance to methotrexate (Wigler, et al., Proc. Natl. Acad. Sci USA, 77:3567, 1980; O'Hare, et al, Proc. Natl. Acad. Sci. USA, 8:1527, 1981); gpt, which confers resistance to mycophenolic acid (Mulligan & Berg, Proc. Natl. Acad. Sci. USA, 78:2072, 1981; neo, which confers resistance to the aminoglycoside G-418 (Colberre-Garapin, et al., J. Mol. Biol., 150:1, 1981); and hygro, which confers resistance to hygromycin (Santerre, et al., Gene, 30:147, 1984) genes. Recently, additional selectable genes have been described, namely trpB, which allows cells to utilize indole in place of tryptophan; hisD, which allows cells to utilize histinol in place of histidine (Hartman & Mulligan, Proc. Natl. Acad. Sci. USA, 85:8047, 1988); and ODC (ornithine decarboxylase) which confers resistance to the ornithine decarboxylase inhibitor, 2-(difluoromethyl)-DL-ornithine, DFMO (McConlogue L., In: Current Communications in Molecular Biology, Cold Spring Harbor Laboratory, ed., 1987).

Microbially or eukaryotically expressed peptides of the invention may be isolated and/or purified using any art-known means such as, for example, preparative chromatographic separations and immunological separations such as those involving the use of monoclonal or polyclonal antibodies or antigens.

The compounds described herein can be produced by the methods described above and also by covalently linking the tumor-binding peptide to the additional domains, e.g., the detectable moieties, the capture reagents, the therapeutic agents, and/or the drug binding domains that bind to a drug or biologic agent. Tumor-binding peptides (e.g., the vimentin-binding and collagen-binding peptides), can be separately produced, e.g., by expression of a recombinant nucleic acid encoding the peptide or by chemical synthesis as described above, or by a combination of the two. The linkers described herein can be separately produced by expression of a recombinant nucleic acid encoding the linker or by chemical synthesis or can be expressed with the tumor-binding peptide, as described previously. One of the one or more linkers can be attached on the N- or C-terminal end of the peptide. In some cases the linker can comprise a cysteine residue such that the cysteine residue is the terminal residue. It is then possible to react the thiol group of the terminal cysteine residue with a maleimide-group to form a covalent linkage. Additional domains can be linked to the end of the peptides through other known covalent interactions.

Methods of Using the Tumor-Targeting Compounds

The compounds and pharmaceutical compositions described herein can be useful for the treatment or diagnosis of a disease (e.g., cancer or viral infection), for detecting cancer cells in a sample (e.g., CTCs), and/or for isolating, purifying or removing CTCs from a sample and/or from a subject's circulation.

Use of Targeted-Compounds in the Detection of Cancer Cells

Provided herein are methods of detecting cancer cells, tumors, and CTCs that have exposed vimentin and/or collagen. The CTCs are detected by contacting a sample comprising the CTCs with a compound described herein. The vimentin-binding peptide of the described compounds binds the compound to the CTC. In some embodiments, the third domain of the compounds comprises a detectable moiety. This moiety can be an agent known in the art that is capable of ready detection by means known in the art, including for example, a radioactive isotope, a magnetic compound, an x-ray absorber, a fluorescent molecule, a chemical compound, or a biological tag, or any combination thereof. The vimentin-binding peptide localizes the compound to the surface of the CTCs and so the detectable moiety of the compound is detected on the surface of the CTCs. In some cases, the vimentin-binding peptide and a collagen-binding peptide localizes the compound to the surface of the CTCs. These dual-targeted compounds may facilitate broad-spectrum detection of cancer cells.

Due to the selective targeting capabilities, the tumor-binding peptides (e.g., the vimentin and/or the collagen targeting peptides) can be used to detect cancer cells, tumors, and/or CTCs. These methods can facilitate the detection of metastatic cancers in subjects, e.g., those who have been diagnosed as having cancer, or the detection of cancer cells in subjects who have not been previously diagnosed as having cancer. The compounds also facilitate early detection, assessment, and treatment of cancer in subjects. The detection can be performed on both liquid and non-liquid samples, including, for example, biological samples such as tissue, blood (e.g., blood biopsy), urine, serum, bone marrow, and/or cerebral spinal fluid. In some cases, the detection, diagnosis, or prognosis is performed on a liquid biopsy.

The compounds described herein can be used, for example, to detect CTCs in a blood sample from a subject. The detection includes contacting the sample with the compound. In some embodiments, the sample is purified or modified prior to contacting with the compounds. For example, a blood sample can be depleted of CD45+ cells prior to detecting the CTCs.

The methods of detecting CTCs described herein include (i) administering the compounds in vivo, or contacting a sample with the compounds ex vivo or in vitro; and (ii) detecting the compounds, thereby detecting the CTCs.

Use of the Targeted-Compounds in the Diagnosis and Prognosis of Cancers

The present specification provides methods of diagnosing cancer using the vimentin-binding compounds described herein. The compounds can be useful in the early diagnosis of metastatic cancer, as these methods can detect the CTCs before the cancer has formed a secondary tumor. The methods described herein can facilitate monitoring the progression of a cancer, the efficacy of a cancer treatment, and/or determining the stage of a cancer.

The methods described herein for the diagnosis or prognosis a disease are also helpful in that they do not require a tissue biopsy or invasive procedures. Rather, a liquid biopsy is easy and safe to perform, and multiple samples can be taken over time and/or can be easily repeated.

Included herein are methods for diagnosing a cancer that include obtaining a sample from a subject, and determining the presence and/or level of CTCs in the sample. The presence and/or level of CTCs in the sample can be compared with the presence and/or level of CTCs in one or more references, e.g., a control reference that represents a normal level and/or a disease reference that represents a level of CTCs associated with a particular stage or progression of cancer. The reference level can be a preselected reference level or threshold.

The presence and/or level of the CTCs can be determined using compounds described herein with methods known in the art, e.g., using quantitative methods to detect the detectable moiety. In some embodiments, high throughput methods known in the art can be used to detect the presence and/or level of the compound.

Suitable reference values can be determined using methods known in the art, e.g., using standard clinical trial methodology and statistical analysis. The reference values can have any relevant form. In some cases, the reference comprises a predetermined value for a meaningful level of CTCs, e.g., a control reference level that represents a normal level of CTCs, e.g., a level in an unaffected subject or a subject who is not at risk of developing a disease described herein, e.g. cancer.

The predetermined level can be a single cut-off (threshold) value, such as a median or mean, or a level that defines the boundaries of an upper or lower quartile, tertile, or other segment of a clinical trial population that is determined to be statistically different from the other segments. It can be a range of cut-off (or threshold) values, such as a confidence interval. It can be established based upon comparative groups, such as where association with risk of developing disease or presence of disease in one defined group is a fold higher, or lower, (e.g., approximately 2-fold, 4-fold, 8-fold, 16-fold or more) than the risk or presence of disease in another defined group. It can be a range, for example, where a population of subjects (e.g., control subjects) is divided equally (or unequally) into groups, such as a low-risk group, a medium-risk group and a high-risk group, or into quartiles, the lowest quartile being subjects with the lowest risk and the highest quartile being subjects with the highest risk, or into n-quantiles (i.e., n regularly spaced intervals) the lowest of the n-quantiles being subjects with the lowest risk and the highest of the n-quantiles being subjects with the highest risk.

In some embodiments, the predetermined level is a level or occurrence in the same subject, e.g., at a different time point, e.g., an earlier time point. Subjects associated with predetermined values are typically referred to as reference subjects. For example, in some embodiments, a control reference subject does not have a disorder described herein (e.g., cancer). A disease reference subject is one who has (or has an increased risk of developing) cancer. An increased risk is defined as a risk above the risk of subjects in the general population.

Thus, in some cases the level of CTCs in a subject being greater than or equal to the reference level of CTCs is indicative of the presence of cancer or increased risk of developing cancer. In some embodiments, the amount by which the level in the subject is the higher or less than the reference level is sufficient to distinguish a subject from a control subject, and optionally is a statistically significantly higher or less than the level in a control subject. In cases where the level of CTCs in a subject being equal to the reference level of CTCs, the "being equal" refers to being approximately equal (e.g., not statistically different).

The predetermined value can depend upon the particular population of subjects (e.g., human subjects) selected. For example, an apparently healthy population will have a different 'normal' range of levels of CTCs than will a population of subjects which have, or are likely to have, cancer. Accordingly, the predetermined values selected may take into account the category (e.g., sex, age, health, risk, presence of other diseases) in which a subject (e.g., human subject) falls. Appropriate ranges and categories can be selected with no more than routine experimentation by those of ordinary skill in the art. In characterizing likelihood, or risk, numerous predetermined values can be established.

Use of the Targeted-Compounds in Detecting Viruses

Provided herein are methods of using the targeted-compounds for detecting and/or removing viruses, or treating viral infections. The compounds described herein comprise a vimentin-binding peptide that selectively binds to vimentin with high-affinity. This binding peptide can mimic the sequence of vimentin that is also recognized by viral capsid and membrane proteins for entry of the virus into a cell. In some embodiments, the peptides can be derived from the regions and sequences of viral proteins that interact with vimentin. Therefore these binding peptides can also target viral proteins.

The methods described herein include the use of the compounds to target viral particles or proteins. The compounds can include (i) a detectible moiety, (ii) an anti-viral drug or an anti-viral drug binding domain, or (iii) a capturing reagent. Therefore, the compounds can be used for detecting the viruses, targeting or binding an anti-viral to the viruses, or removing the viruses.

Use of Targeting-Compounds in Treating Cancer

Compounds described herein can be used for the treatment of a disease, for example, cancer and/or tumors. The cancer can be, e.g., a primary or metastatic cancer, including but not restricted to, colorectal cancer, breast cancer, brain tumors, non-small cell lung cancer, pancreatic cancer, prostate cancer, sarcoma, carcinoma, and/or melanoma. The cancer can be, e.g., cancer of the stomach, melanoma, colon, rectum, mouth/pharynx, esophagus, larynx, liver, pancreas, lung, breast, cervix uteri, corpus uteri, ovary, prostate, testis, bladder, skin, bone, kidney, brain/central nervous system, head, neck and/or throat; gliomas, sarcoma, or choriocarcinoma. In some cases, the cancer can be, e.g., CTCs of mesodermal origin (e.g. sarcomas), as well as epithelioid CTCs that are undergoing an epithelial-to-mesenchymal transition (EMT). In general, the methods of treating cancer can include administering to a subject having cancer an amount of the compound or pharmaceutical composition sufficient to treat cancer in the subject.

An exemplary method of treating cancer in a subject using the compound can include: (i) providing an anti-cancer agent; (ii) providing a compound that includes (a) a vimentin-binding peptide, (b) a linker, and (c) a drug binding domain that binds to the anti-cancer agent; (iii) mixing the anti-cancer agent with the compound at a specific ratio under desired conditions for a sufficiently long period to allow association of the compound with the anti-cancer agent, thereby forming an anticancer agent/compound complex; and (iv) administering to a subject in need of treatment an effective amount of a pharmaceutical composition comprising the anticancer agent/compound complex. The conditions for the mixing step can be optimized based on (i) the solubility and stability of the anticancer agent, (ii) the solubility and stability of the compound, and/or (iii) the N-terminal and C-terminal modifications of the compound. For example, the mixing step can be performed in phosphate buffered saline (PBS) at 30° C. for 30 min.

In some embodiments, the subject is a human. In some embodiments, the cancer is a solid tumor, for example, a sarcoma, a carcinoma, or a melanoma. In some embodiments, the compounds are used to treat circulating tumor cells. Also provided herein are methods of administering a compound that includes both the vimentin-binding peptide and a collagen-binding peptide. Exposed collagenous proteins are present in pathological areas, including cancerous lesions (e.g., primary tumors and metastatic lesions), and therefore the dual-binding (vimentin- and collagen-binding) compounds can deliver anti-cancer agents to solid tumors in addition to the CTCs.

Provided are methods of treating cancer with compounds described herein, e.g., those that comprise (i) a drug binding domain and/or (ii) a drug or biologic agent covalently linked to the linker. The drug can be, e.g., a cytotoxic or cytostatic agent used for chemotherapy (e.g., a chemotherapeutic agent), a monoclonal antibody, growth factor, RNA, or siRNA. The drug-binding domain can comprise, e.g., sequences that bind directly or indirectly to a particular class of chemotherapeutic or biologic agents, for example, paclitaxel, monoclonal antibodies, growth factors, or small interfering RNA (siRNA).

The drug can be an angiogenesis modulating agent, e.g., for directly or indirectly affecting endothelial cell and/or tumor cell proliferation. The angiogenesis modulating agent can be, e.g., selected from: growth factors including vascular endothelial growth factor (VEGF), epidermal growth factor (EGF), hepatocyte growth factor (HGF), platelet derived endothelial cell growth factor (PD-ECGF), platelet derived growth factor (PDGF); insulin-like growth factor (IGF), interleukin-8, growth hormone, angiopoietin, acidic and basic fibroblast growth factors (FGFs), transforming growth factor alpha (TGF-alpha.), an enzyme, an enzymatic inhibitor, and/or an antibody specific for these growth factors and their receptors. In some embodiments, the angiogenesis modulating agent is a monoclonal antibody (mAb). In some embodiments, the angiogenesis modulating agent is directed against VEGF or specifically binds VEGF, for example, the angiogenesis modulating agent can be bevacizumab, aflibercept, or rilonacept. In some embodiments, the angiogenesis modulating agent is a chemotherapeutic agent used in a metronomic regimen to induce anti-angiogenesis.

The drug binding domain can be a chemotherapeutic agent binding domain. For example, the chemotherapeutic agent binding domain can be a domain that binds a chemotherapeutic agent such as paclitaxel, docetaxel, and/or nab-paclitaxel. The binding domain can be one that binds a mAb, e.g., a mAb that is selected from the group consisting of an anti-CTLA-4, anti-PD-1, and anti-PD-L1 antibody. Exemplary mAbs include ipililumab, nivolumab, pembrolizumab, or any combination thereof. The drug or biologic agent can be an siRNA. For example, the siRNA-binding domain can comprises the sequence of SEQ ID NO: 45 and/or SEQ ID NO: 46 (RRRRRRRRR (SEQ ID NO: 45) and/or (D-Arg)(D-Arg)(D-Arg)(D-Arg)(D-Arg)(D-Arg)(D-Arg)(D-Arg)(D-Arg) (SEQ ID NO: 46)). Other drug binding domains are known in the art, for example, see WO 2016/054107, which is incorporated herein in its entirety.

In some embodiments, treating cancer comprises removing the CTCs from circulation of the subject. For example, when working with only vimentin-binding domains, the vimentin-binding domain can be immobilized on a solid support (e.g., in one or more columns) and blood from the subject can be passed over the solid support, e.g., in an apheresis device or column, such that the CTCs stick to the vimentin-binding domains to thereby remove the CTCs from a subject's bloodstream. The blood from the subject may then be returned to the subject. Alternatively, the compound comprises a vimentin-binding domain, a linker, and a capture reagent, wherein the capture reagent binds to the solid support such that the compound is immobilized on a solid support, blood from the subject is passed over the solid support, and the CTC-depleted blood is returned to circulation in the subject. Similarly, the compounds described herein can be immobilized on a resin. In some embodiments the compound comprises a vimentin-binding peptide and the compound is immobilized on a resin. Additionally, the compounds described herein can be associated with a solid support, a chromatography column, or an apheresis device.

Use of the Targeted-Compounds in Isolating CTCs

The compounds described herein can be useful for the isolation, purification, or removal of CTCs. The methods described herein for the isolation and/or purification of CTCs can be useful for the analysis and characterization of CTCs and their microenvironments. Additionally, the removal of CTCs may be useful in the treatment of cancer, as described above. The methods described herein comprise (a) contacting a sample with a compound wherein the compound comprises (i) a first domain comprising a vimentin-binding peptide, (ii) a second domain comprising a linker, and (iii) a third domain comprising a capture reagent, thereby forming a mixture; and (b) contacting the mixture with an immobilizing agent, wherein the immobilizing agent binds to the capture reagent; thereby isolating the CTCs from the sample. The immobilizing agent can be attached to a solid support or the immobilizing agent can be attached to a solid support after binding to the capture reagent. For example, the immobilizing agent can be streptavidin bound to a solid support (e.g., a column or membrane) and the capture reagent can be biotin. As another example, the immobilizing agent can be attached to a magnetic bead, such that a magnetic force can be applied to the mixture after the capture reagent has bound to the immobilizing agent and the compound can be isolated from the sample.

In some embodiments, before the sample is contacted with the compound, the sample is purified or modified, for example, a purification step, chromatography or other means of separating the components of the sample prior to removal of the CTCs. For example, the sample is a blood sample and the CD45+ cells are removed from the sample, or size chromatography is performed on the sample to remove non-CTC cells or to enrich the sample for CTCs.

The methods described herein further provide for accumulating CTCs in a solution for further characterization and study. The CTCs can be characterized using techniques known in the art, including but not limited to: genetic analysis, proteomic analysis, metabolomic and transcriptomic analysis. In addition to flow cytometry and immunocytochemical analysis of specific cell and tumor markers, PCR-based sequencing techniques can identify specific mutations, biomarkers, and specific receptor expression that can predict drug responsiveness and resistance. Characterization of CTCs can include, for example, detection of cyclin-G1 over-expression, cytogenetic and molecular genetic analyses for chromosomal translocations, transcriptional analysis of FGF8 and NPM3, molecular analysis for presence of TGFBR3 and MGEA5 rearrangements, molecular analysis for presence of miR-122 micro-RNA, detection of EWSR1 gene translocations, and/or molecular analysis of cell surface proteins.

As with the compounds described herein, the compound used in the methods of purifying, isolating, or removing the CTCs can also include a collagen-binding peptide.

The compounds described herein can be used, e.g., on a resin for binding or isolating CTCs. A resin can comprise, e.g., a compound described herein where the compound comprises a first domain of vimentin-binding peptide and the compound is immobilized on the resin. Additionally, the resin can comprise a second domain comprising a linker wherein the compound is immobilized on the resin via the linker. In some embodiments the resin also includes a third domain that comprises an exposed collagen binding peptide and a fourth domain that is a second linker. The collagen- and vimentin-binding peptides can be linked by a linker and form a dual-binding peptide. The dual-binding or dual-targeting peptide can then be immobilized on the resin by another linker.

Resins described herein can be used as a solid support for purification and/or isolation of CTCs using methods known in the art for purifying and isolating agents using affinity resins. For example, the resins can be used in apheresis devices, chromatography apparatuses (e.g., chromatography and/or affinity columns), and/or filtration devices. Additionally, the compounds described herein can be immobilized directly on the solid support, for example, a compound comprising a vimentin-binding peptide can be directly bound to a solid support or may be linked via a linker domain. In some cases the solid support (e.g., resins, beads, etc.) can comprise a plurality of immobilized vimentin binding domains and/or compounds described herein.

As described above, the removal of CTCs from a sample can be useful in the treatment of cancer, e.g., by the removal of CTCs from circulation of a subject. The compounds, resins, solid supports, and columns described herein can be configured for use in an apheresis device or a device used for filtration of blood in circulation of a subject. The method of treating cancer by removing CTCs from circulation can also include administering a compound that includes a drug or a drug-binding domain, as described herein. The methods may also include administering an additional therapeutic agent.

Methods of Screening for Agents that Bind to Vimentin

The compounds described herein are also useful in the screening for agents or test compounds, e.g., peptides, polynucleotides, inorganic or organic large or small molecule test compounds that bind to vimentin. An exemplary method of screening for agents that bind to vimentin can include: (i) providing a test agent; (ii) contacting the test agent with one or more of the compounds described herein; (iii) identifying the test agent(s) that binds to the compound, thereby identifying an agent that binds to vimentin.

As used herein, "small molecules" refers to small organic or inorganic molecules of molecular weight below about 3,000 Daltons. In general, small molecules useful for the invention have a molecular weight of less than 3,000 Daltons (Da). The small molecules can be, e.g., from at least about 100 Da to about 3,000 Da (e.g., between about 100 to about 3,000 Da, about 100 to about 2500 Da, about 100 to about 2,000 Da, about 100 to about 1,750 Da, about 100 to about 1,500 Da, about 100 to about 1,250 Da, about 100 to about 1,000 Da, about 100 to about 750 Da, about 100 to about 500 Da, about 200 to about 1500, about 500 to about 1000, about 300 to about 1000 Da, or about 100 to about 250 Da).

The test compounds can be, e.g., natural products or members of a combinatorial chemistry library. A set of diverse molecules should be used to cover a variety of functions such as charge, aromaticity, hydrogen bonding, flexibility, size, length of side chain, hydrophobicity, and rigidity. Combinatorial techniques suitable for synthesizing small molecules are known in the art, e.g., as exemplified by Obrecht and Villalgordo, Solid-Supported Combinatorial and Parallel Synthesis of Small-Molecular-Weight Compound Libraries, Pergamon-Elsevier Science Limited (1998), and include those such as the "split and pool" or "parallel" synthesis techniques, solid-phase and solution-phase techniques, and encoding techniques (see, for example, Czarnik, Curr. Opin. Chem. Bio. 1:60-6 (1997)). In addition, a number of small molecule libraries are commercially available. A number of suitable small molecule test compounds are listed in U.S. Pat. No. 6,503,713, incorporated herein by reference in its entirety.

Libraries screened using the methods of the present invention can comprise a variety of types of test compounds. A given library can comprise a set of structurally related or unrelated test compounds. In some embodiments, the test compounds are peptide or peptidomimetic molecules. In some embodiments, the test compounds are nucleic acids. In some embodiments, the test compounds and libraries thereof can be obtained by systematically altering the structure of a first test compound, e.g., the vimentin-binding peptides described herein.

Pharmaceutical Compositions, Dosage Regimen, and Methods of Administration of the Tumor-Targeted Compounds Provided herein are pharmaceutical compositions comprising one or more of the compounds described herein and methods of manufacturing the same. The compositions can further include one or more therapeutic and/or biologic agents. Additionally, pharmaceutical compositions typically include a pharmaceutically acceptable carrier. As used herein the language "pharmaceutically acceptable carrier" includes saline, solvents, dispersion media, coatings, antibacterial and antifungal agents, isotonic and absorption delaying agents, and the like, compatible with pharmaceutical administration.

The active ingredient of a pharmaceutical composition can be formulated for delivery by any available route including, but not limited to parenteral (e.g., intravenous), intradermal, subcutaneous, oral, nasal, bronchial, ophthalmic, transdermal (topical), transmucosal, rectal, and vaginal routes. A pharmaceutical composition provided herein can include another delivery agent and a pharmaceutically acceptable carrier. As used herein the term "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into pharmaceutical formulations that contain an antibody or antigen-binding fragment thereof as described herein.

Methods of formulating suitable pharmaceutical compositions are known in the art, see, e.g., Remington: The Science and Practice of Pharmacy, 21st ed., 2005; and the books in the series Drugs and the Pharmaceutical Sciences: a Series of Textbooks and Monographs (Dekker, N.Y.). For example, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injection can include sterile aqueous solutions (where water soluble), dispersions, and sterile powders for the extemporaneous preparation of sterile injectable solutions or dispersion. For intravenous administration, suitable carriers include physiological saline, bacteriostatic water, Cremophor EL™ (BASF, Parsippany, N.J.), or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, the preferred methods of preparation are vacuum drying and freeze-drying, which yield a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring.

For administration by inhalation, the compounds can be delivered in the form of an aerosol spray from a pressured container or dispenser that contains a suitable propellant, e.g., a gas such as carbon dioxide, or a nebulizer. Such methods include those described in U.S. Pat. No. 6,468,798.

Certain tumors may be accessible by administration by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In some embodiments, the therapeutic compounds can be prepared with carriers that will protect the therapeutic compounds against rapid elimination from the body, such as a controlled release formulation, including implants and microencapsulated delivery systems.

In some embodiments, the pharmaceutical composition can be directly administered to the areas of active angiogenesis. In some embodiments, the pharmaceutical composition can be administered through conventional routes, e.g., intravenously. Microencapsulation technology or liposomes can be used to protect the pharmaceutical compositions during circulation and release them at the site of active angiogenesis.

The pharmaceutical compositions can be included in a container, pack, or dispenser together with instructions for administration.

The therapeutic and/or biologic agents can be administered in an effective amount, at dosages and for periods of time necessary to achieve the desired result. An effective amount can be administered in one or more administrations, applications or dosages. A therapeutically effective amount of a pharmaceutical composition (i.e., an effective dosage) depends on the pharmaceutical composition selected. The compositions can be administered from one or more times per day to one or more times per week; including once every other day. The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of the pharmaceutical compositions described herein can include a single treatment or a series of treatments.

Dosage regimens can be adjusted to provide the optimum therapeutic response. For example, several divided doses can be administered daily or the dose can be proportionally reduced as indicated by the exigencies of the therapeutic situation. Those skilled in the art will be aware of dosages and dosing regimens suitable for administration of the new monoclonal antibodies disclosed herein or antigen-binding fragments thereof to a subject. See e.g., Physicians' Desk Reference, 63rd edition, Thomson Reuters, Nov. 30, 2008. For example, Dosage, toxicity and therapeutic efficacy of the therapeutic compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Kits

Also provided are kits that include one or more of the compounds described herein. Kits generally include the following major elements: packaging, reagents comprising binding compositions as described above, optionally a control, and instructions. Packaging can be a box-like structure for holding a vial (or number of vials) containing said binding compositions, a vial (or number of vials) containing a control, and instructions for use in a method described herein. Individuals skilled in the art can readily modify the packaging to suit individual needs.

In some embodiments, a kit provided herein can include at least one (e.g., one, two, three, four, five, or more) composition containing at least one (e.g., one, two, three, four, five, or more) of the compounds described herein, and at least one (e.g., one, two, three, four, five, or more) other composition in a separate vial containing a therapeutic or biologic agent known in the art to be effective in treating cancer. In some embodiments, a kit provided herein can include the compounds described herein immobilized on a solid support. In another embodiment, the kit can include the compounds described herein and at least one other composition containing reagents for a colorimetric assay.

Compositions and kits as provided herein can be used in accordance with any of the methods (e.g., treatment methods) described above. For example, compositions and kits can be used to treat cancer. Those skilled in the art will be aware of other suitable uses for compositions and kits provided herein, and will be able to employ the compositions and kits for such uses.

EXAMPLES

The invention is further described in the following examples, which do not limit the scope of the invention described in the claims.

Example 1: Design and Analysis of Vimentin-Binding Sequences to Target CTCs

The pericellular matrix (PCM) or glycocalyx of CTCs is composed of (i) hyaluronic acid, an anionic polymer of disaccharide repeats, bound to the cell membrane by specific hyaluronan receptors (e.g., CD44) and extending into the extracellular space; (ii) sulfated proteoglycans, including chondroitin sulfate and heparin sulfate; and (iii) various adhesive proteins and fibrils, which may include vimentin, specific types of collagens, and even von-Willebrand factor (vWF), depending on the CTC phenotype and association with circulating platelets (FIG. 1A). The presence of exposed collagens (XC-proteins) and/or exposed vimentin (XV-protein) within the PCM of sarcoma CTCs and CTCs undergoing an epithelial-to-mesenchymal transition (EMT) is of considerable diagnostic importance; thereby providing strategic target proteins for compounds designed to detect, isolate, characterize and/or capture CTCs based on XC-proteins (FIG. 1B) and/or XV-proteins (FIG. 1C) within the PCM. As shown in FIGS. 1B and 1C, the compounds can include (1) a high-affinity target protein binding domain; (2) a customized flexible linker segment to optimize protein-protein interactions while avoiding steric hindrance and torsional strain; and (3) a capture (e.g., Biotin) or reporter (e.g., FITC) or therapeutic (e.g., anti-cancer drug or drug-binding domain) molecule.

Vimentin is a type III intermediate filament (IF) protein that is expressed in normal mesenchymal cells, in sarcoma CTCs, and in CTCs that have undergone EMT in the course of metastatic progression. As shown in FIG. 2, the vimentin monomer has a central alpha-helical Rod domain, comprised of two distinctive Coil regions (designated 1A, 1B and 2A, 2B) capped on each end by non-helical amino (Head) and carboxyl (Tail) domain. Two nascent vimentin monomers self-assemble into a coiled-coil dimer, which is the basic subunit of subsequent self-assembly: then into staggered anti-parallel tetramers, and further into protofibrils and unit-length filaments, which are able to anneal to each other end-to-end to form the intermediate filaments. Highly conserved domains and/or secondary structures that were known to play important roles in the molecular forces and dynamics governing vimentin self-assembly and disassembly were indicated in FIG. 2 as circular shading. The primary structures of these critical conserved domains, involved in powerful protein-protein interactions, were selected to serve as experimental probes for the development of high-affinity vimentin-binding peptides that are of considerable clinical utility in the characterization and/or capture of VIM+ CTCs, as well as targeted cancer therapies.

In view of this primary structure analysis, 15 vimentin-binding or vimentin- and collagen-binding peptides were designed, synthesized, and biotin or FITC were covalently linked to the terminus of the peptides. For example, SEQ ID NOs: 1, 2, 4, 9, 11, and 14 were designed to target vimentin and include a FITC label on the C-terminus of the peptide for detection of the peptide. SEQ ID NOs: 3, 5, 6, 10, 12, and 15 were designed to target vimentin and include a biotin capture reagent for capturing, isolating, purifying, or removing the CTCs. SEQ ID NOs: 7 and 8 target both vimentin and collagen, while SEQ ID NOs: 13, 19, 20, and 21 target only collagen.

The vimentin-binding peptides were designed to interact with the various domains of vimentin including the highly conserved domains and/or secondary structures (shaded in FIG. 2).

Example 2: Design and Analysis of Vimentin-Binding Sequences Based on Interactions with Viruses Viruses exploit cellular machinery for various events including viral entry into a cell. The major cellular contributors in this process are the cytoskeletal components, such as microfilaments, microtubules, and vimentin. Vimentin associates directly with outer capsid proteins of viruses, including but not limited to the outer capsid protein VP2 of Bluetongue Virus and the V-3 loop of gp120 envelope protein of HIV-1. The interactions of specific viruses with vimentin during the course of viral infection was used to design additional vimentin-binding aptamers. For example, SEQ ID NOs: 16-18 were designed to mimic the protein-protein interactions of vimentin and the viral proteins at highly conserved sequences (Sirpada and Dayaraj, Cell Health and Cytoskeleton, 23 Mar. 2010. Vol 2010:2 Pgs 1-7; Bhattacharya et al., Virol J., (2007) 4 (1). p. 7; Thomas et al, Viral Immunol. 1996:9(2):73-87; and Jiang et al., Nature Structural & Molecular Biology. 17, 955-961 (2010)). In this manner, the viral protein for vimentin was engineered into the design of a novel vimentin-binding peptide.

Additionally, the vimentin-to-vimentin protein structure and interactions described in Example 1 can be used to design virus-binding peptides, specifically in cases where the vimentin binding site for the particular virus is represented in the structure of the vimentin-aptamer (see shaded areas of FIG. 2).

Example 3: Collagen-Binding and Ni-Chelate Affinity Assays

As shown in FIG. 3, aptamers #7, #9, and #20 (aptamers comprising SEQ ID NOs: 7, 9, and 20, respectively) bind tightly to collagen-agarose beads under stringent washing conditions. Aptamers and reporters were mixed and loaded under mild binding conditions (PBS, pH 7.4), followed by washing with increasing concentrations of salt and/or detergent (PBST, using Tween 20). Stringent washing generally includes 10 column volumes of 1M NaCl in PBST, pH 7.4).

Figure 4:
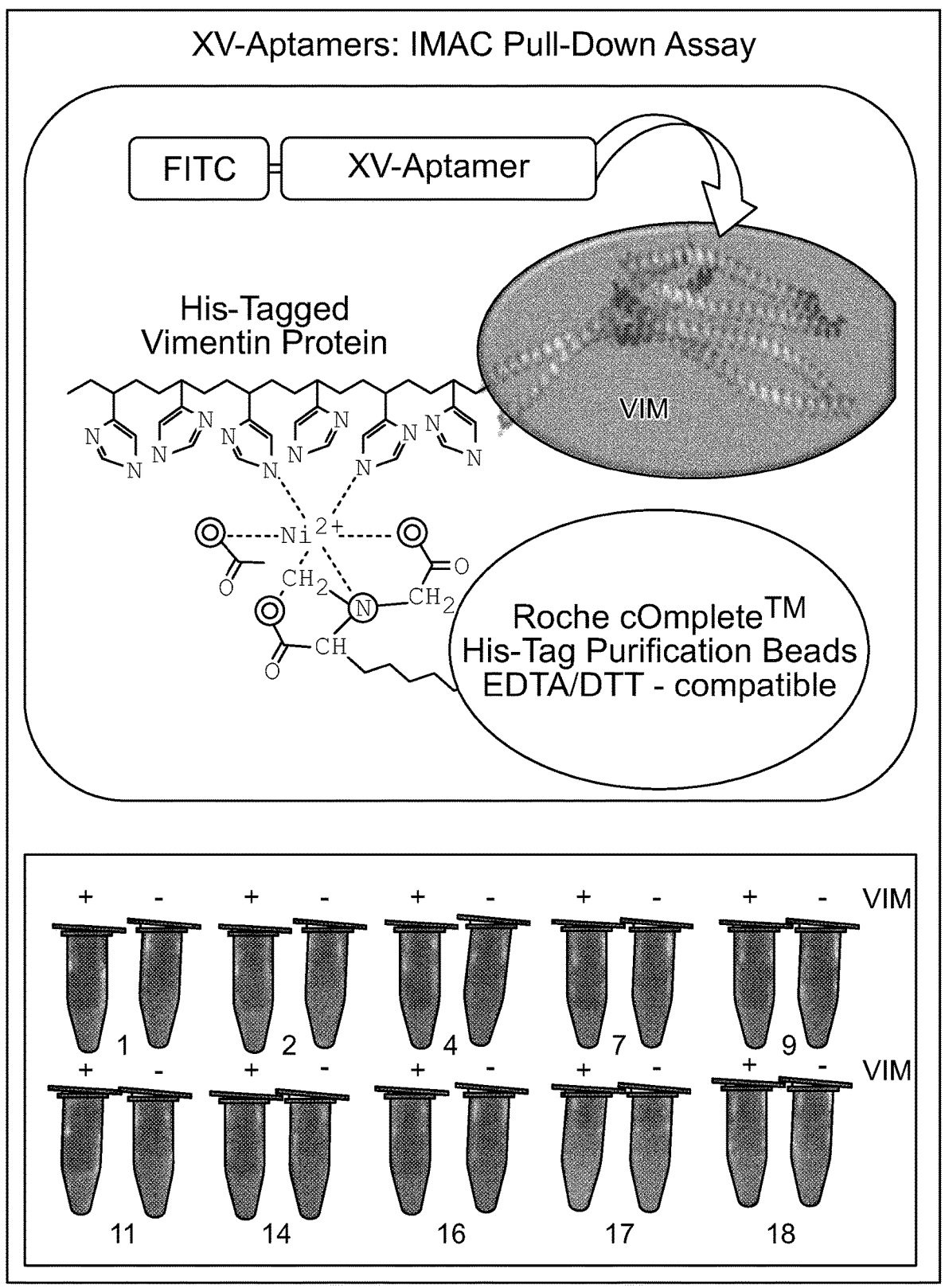
FIG. 4 is a schematic and photograph of a IMAC Pull-down assay. The numbers 1, 2, 4, 7, 9, 11, 14, 16, 17, and 18 under the tubes correspond to aptamers consisting of SEQ ID NOs: 1, 2, 4, 7, 9, 11, 14, 16, 17, and 18, respectively. IMAC=immobilized affinity chromatography/ Ni- or Metal-chelate chromatography.

Aptamers containing VIM binding domains were allowed to associate with purified recombinant His-tagged VIM, followed by the addition of His-Tag beads, which were then used to concentrate the His-VIM and associated aptamers (see FIG. 4). Numbers below the tubes in FIG. 4 reading from left to right, top to bottom, correspond to aptamers that include SEQ ID NOs: 1, 2, 4, 7, 9, 11, 14, 16, 17, and 18, respectively.

Figure 5:
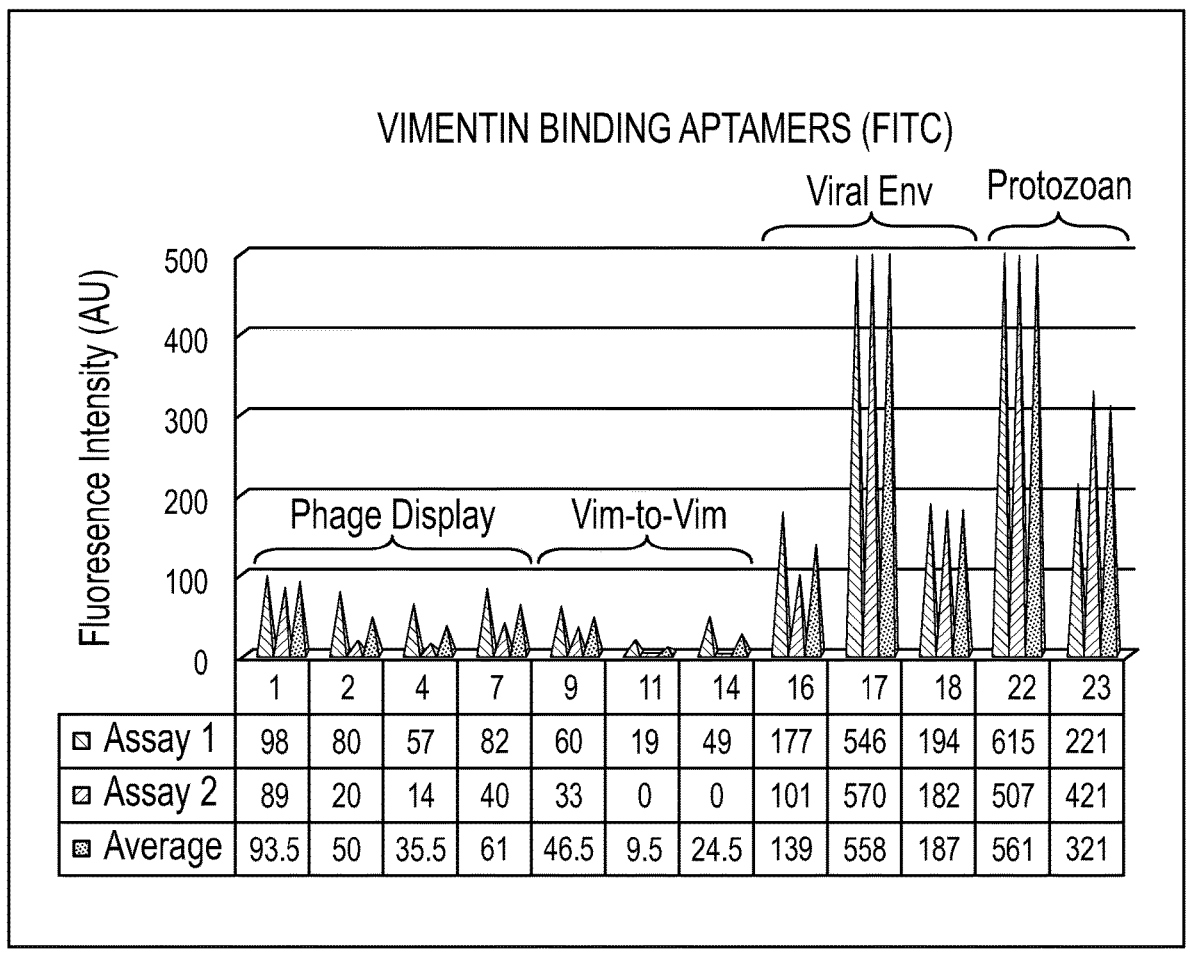
FIG. 5 is a graph showing a comparative evaluation of vimentin-binding aptamers. The numbers 1, 2, 4, 7, 9, 11, 14, 16, 17, 18, 22, and 23 under the graph correspond to aptamers consisting of SEQ ID NOs: 1, 2, 4, 7, 9, 11, 14, 16, 17, 18, 49, and 51, respectively.

The comparative binding efficiency of the aptamers was evaluated by quantifying the net fluorescent signal in the presence and absence of vimentin (e.g., r-vimentin)(see FIG. 5). Numbers 1, 2, 4, 7, 9, 11, 14, 16, 17, 18, 22, and 23 below the graph correspond to aptamers that include SEQ ID NOs: 1, 3, 4, 7, 8, 11, 14, 16, 17, 18, 49, and 51, respectively. VIM-binding sequences from Phage Display studies were positive. Strong binding was seen with aptamers based on specific viral envelope proteins and protozoan proteins (Aptamer #17 (based on HIV), Aptamer #22 (protozoan, SEQ ID NO: 49), and Aptamer #23 (protozoan, SEQ ID NO: 51).

Example 4: Design and Analysis of Anti-VIM Antibodies

Anti-VIM antibodies were produced to define unstructured (linear) epitopes for CTC-binding, detection, targeting, and/or capture.

Figure 6:
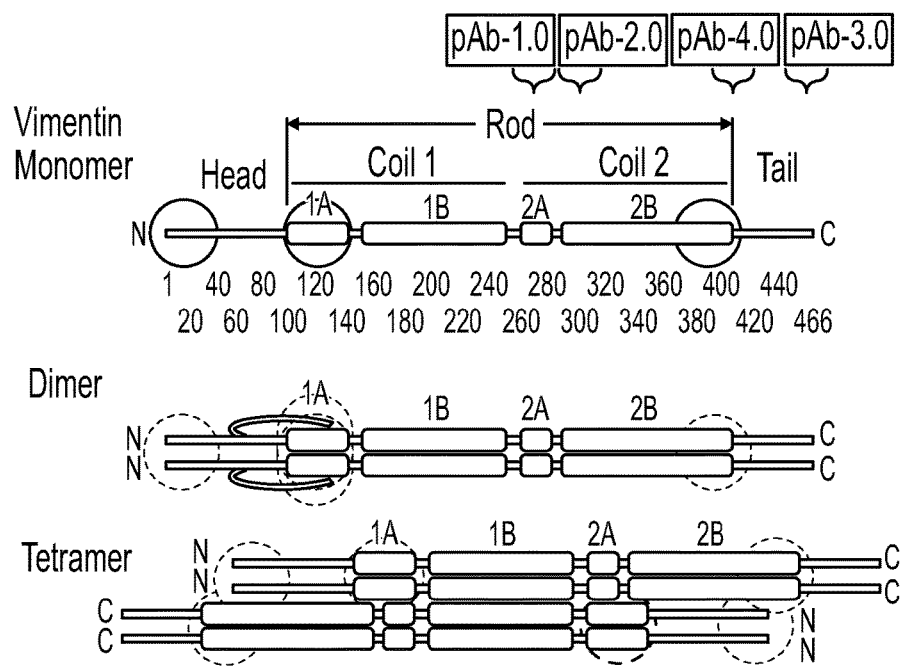
FIG. 6 is a schematic diagram of the design of the sequence-specific polyclonal antibodies. Ab 1.0=SEQ ID NO: 56; Ab 2.0=SEQ ID NO: 57; Ab 3.0=SEQ ID NO: 58; and Ab 4.0=SEQ ID NO: 59.
Figure 7:
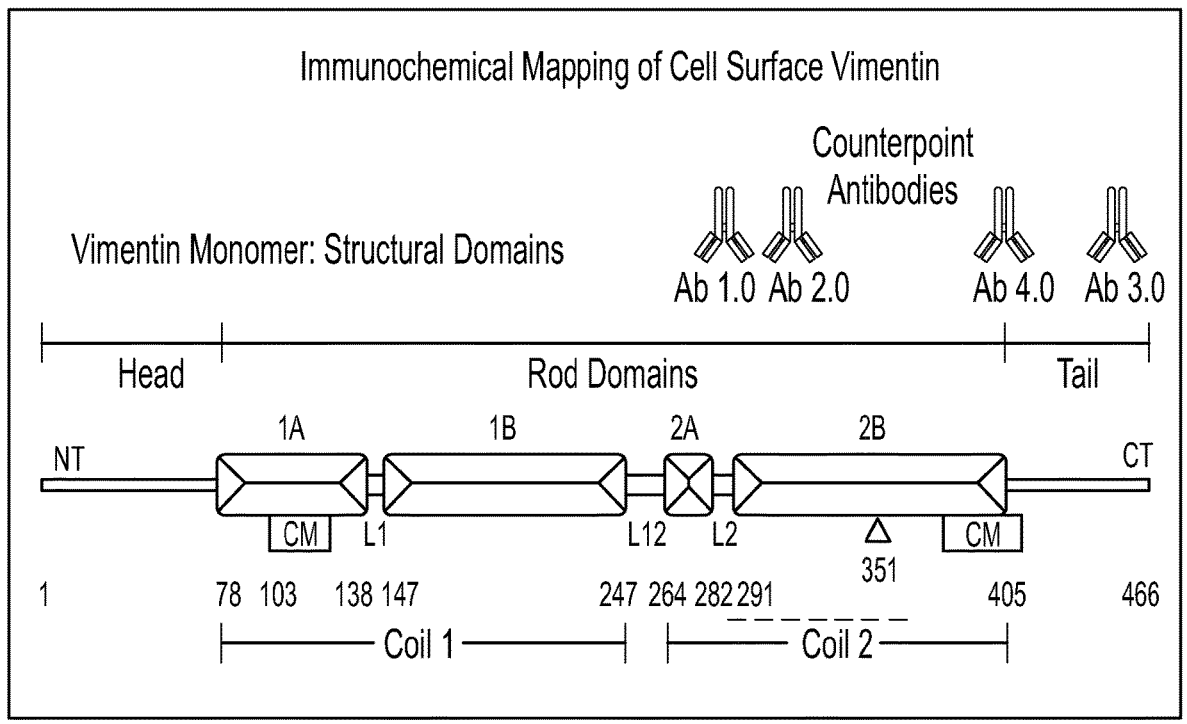
FIG. 7 is a cartoon of the immunochemical mapping of vimentin on the cell surface. Abs 1.0, 2.0, 3.0, and 4.0 are SEQ ID NO: 56, 57, 58, and 59, respectively.

Four sequence specific segments of the human vimentin protein were selected (SEQ ID NO: 56 CGKNLQEAEE-WYKSKFADLSEAANR-amide; SEQ ID NO: 57 CGSEAANRNNDALRQAKQESTEYRR-amide; SEQ ID NO: 58 CGGKTVETRDGQVINETSQHHDDLE-free acid; and SEQ ID NO: 59 KMALDIEIATYRKLLEGEESRISGC) (See FIG. 6 and FIG. 7). Sequence specific polyclonal antibodies (pAbs) were generated in rabbits and were affinity-purified (using the immunizing peptide).

Figure 8:
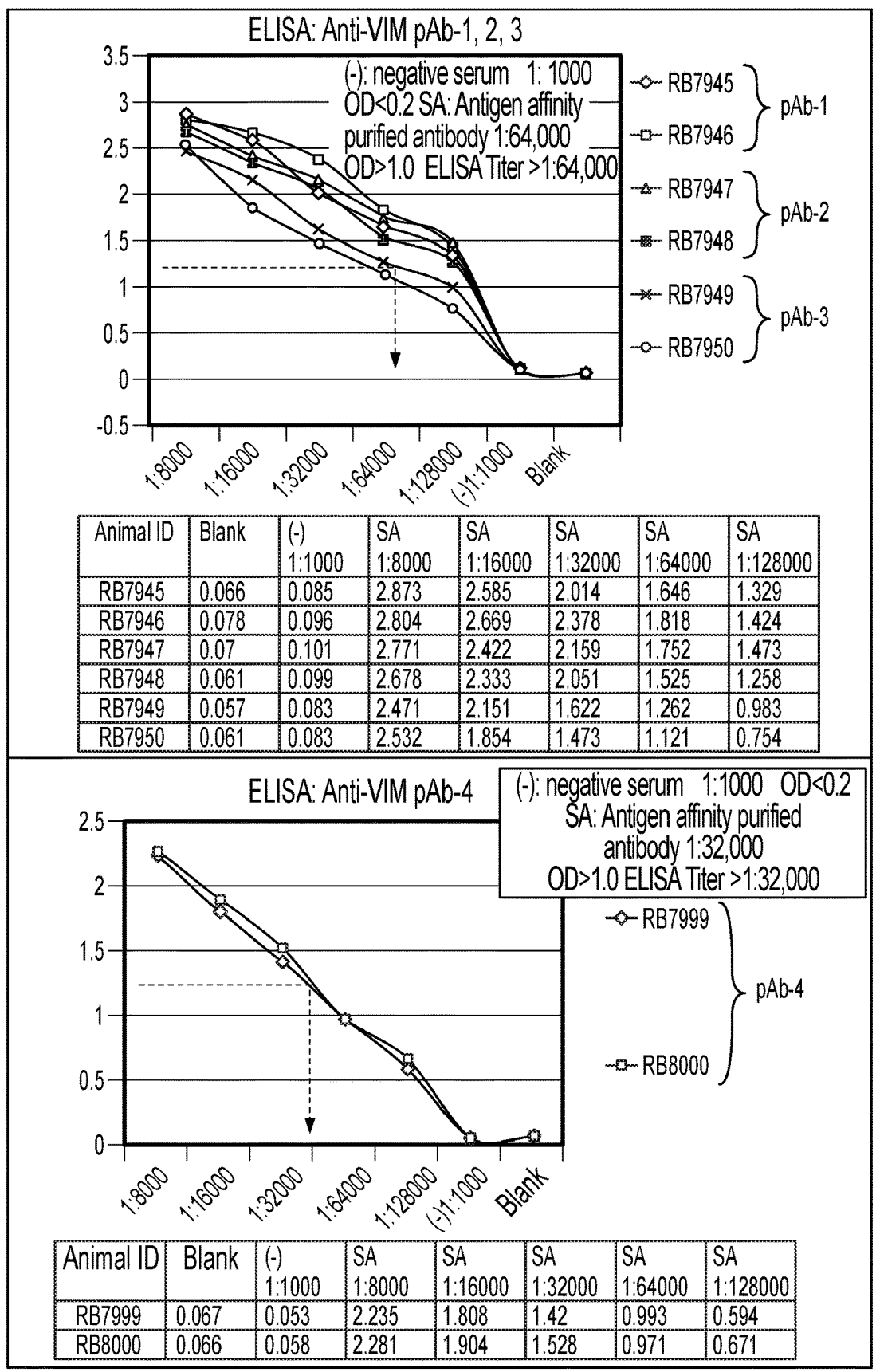
FIG. 8 are graphs showing the titers of the antigen affinity purified anti-VIM antibodies. Top graph shows the titers of Abs 1.0, 2.0, and 3.0. Bottom graph shows the titer of Ab 4.0.
Figure 9:
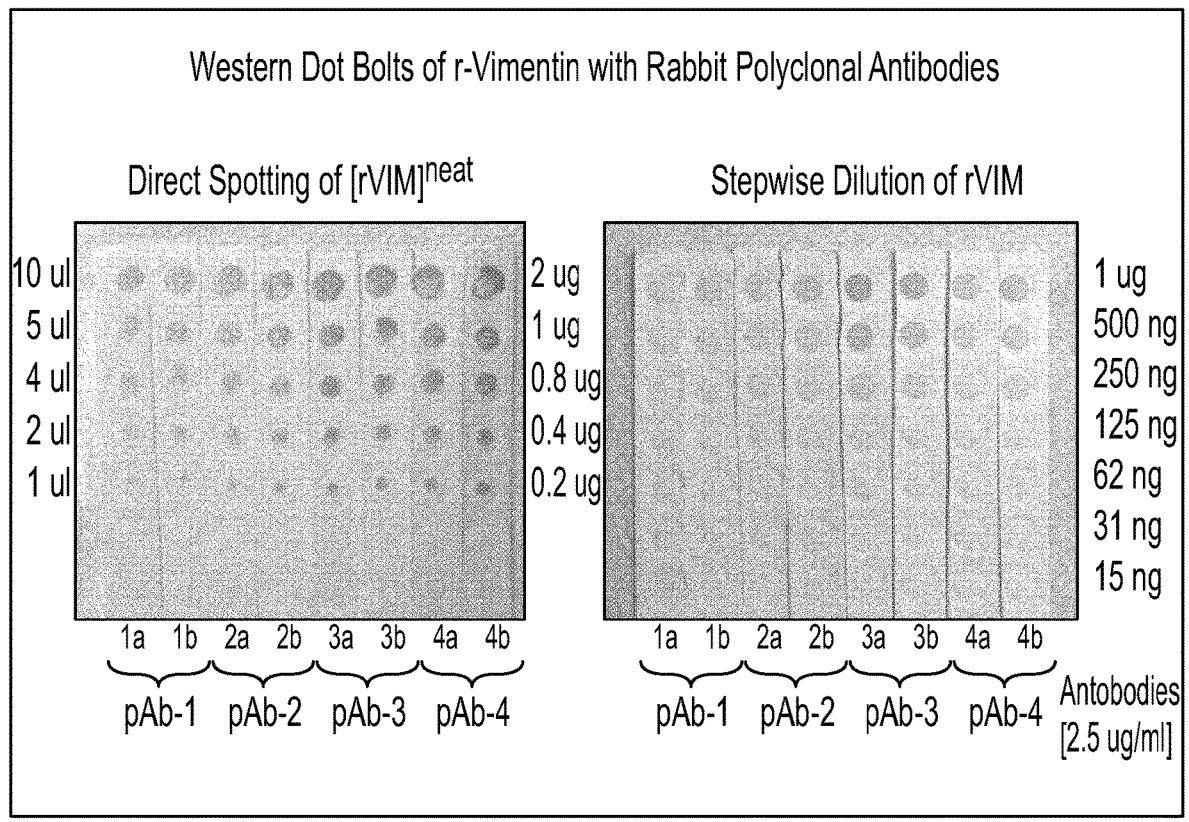
FIG. 9 are western dot blots showing the reactivity of the anti-VIM antibodies on recombinant VIM (e.g., rVIM).

The immune-reactivity of pAbs 1-4 on the respective immunizing peptides were measured and the titers of the respective Abs were determined in an ELISA assay (see FIG. 8). pAb 1, 2, and 3 had titers ≥1:64,000 and pAb 4 had a titer of ≥1:32,000. A Western dot blot confirmed the recognition of full-length vimentin by the various sequence-specific pAbs (see FIG. 9). These sequence specific antibodies were designed as capturing agents for circulating CTCs. All four anti-peptide antibodies recognized recombinant VIM (#3>#4, #2>#1). pAb-3 demonstrated strong affinity towards VIM.

These Abs can be used in in vitro diagnostics, CTC targeting, CTC detection, and CTC treatment. In some cases, these antibodies can be humanized. In some cases, these antibodies can be used to deliver drugs and/or other function moieties to CTCs.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of detecting a tumor in a sample, the method comprising:
   contacting the sample with a compound comprising the amino acid sequence of SEQ ID NO: 17, which comprises:
      a first domain comprising a vimentin-binding peptide;
      a second domain comprising a first linker; and
      a third domain comprising a detectable moiety; and
   detecting the compound and thereby detecting a tumor in the sample.

2. The method of claim 1, wherein the compound binds to tumor cells and wherein detecting the compound comprises detecting the compound bound to tumor cells.

3. The method of claim 1, wherein the compound further comprises:
   a fourth domain that comprises an exposed collagenous (XC) protein binding peptide; and
   a fifth domain that comprises a second linker,
   wherein the XC protein binding peptide and the vimentin-binding peptide are connected via the second linker, thereby forming a dual-binding peptide, and the third domain is connected to the dual-binding peptide via the first linker.

4. The method of claim 1, wherein the sample is a blood sample or blood biopsy.

5. The method of claim 1, wherein contacting the sample with the compound is performed ex vivo, in vivo or in vitro.

6. The method of claim 1, wherein the compound further comprises a human serum albumin (HSA)-binding domain, comprising the amino acid sequence of SEQ ID NO: 47 or SEQ ID NO: 48, linked to one or more of the vimentin-binding peptide, a third linker, and the third domain.

7. The method of claim 3, wherein the exposed collagenous (XC) protein binding peptide is a polypeptide derived from a von Willebrand factor collagen binding domain or a conservative variation thereof that retains collagen binding activity.

8. The method of claim 7, wherein the XC protein binding peptide comprises SEQ ID NO: 22, SEQ ID NO: 23, or SEQ ID NO: 24.

9. The method of claim 3, wherein the XC protein binding peptide binds to XC proteins present in solid tumors or circulating tumor cells (CTCs).

10. The method of claim 1, wherein the compound is PEGylated.

* * * * *

SEQUENCE LISTING

<160> NUMBER OF SEQ ID NOS: 59

<210> SEQ ID NO 1
<211> LENGTH: 12

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Asn Thr Ala Asn Ser Thr Gly Gly Ser Gly Lys
1               5                   10

<210> SEQ ID NO 2
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Val Asn Thr Ala Asn Ser Thr Gly Gly Ser Gly Gly Val Asn Thr Ala
1               5                   10                  15

Asn Ser Thr Gly Gly Ser Gly Lys
            20

<210> SEQ ID NO 3
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Asn Thr Ala Asn Ser Thr Gly Gly Ser Gly Lys
1               5                   10

<210> SEQ ID NO 4
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ser Ala His Gly Thr Ser Thr Gly Val Pro Trp Pro Gly Gly Ser Gly
1               5                   10                  15

Lys

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Ala His Gly Thr Ser Thr Gly Val Pro Trp Pro Gly Gly Ser Gly
1               5                   10                  15

Lys

<210> SEQ ID NO 6
<211> LENGTH: 16
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 6

Xaa Ser Ala His Gly Thr Ser Thr Gly Val Pro Trp Pro Gly Gly Ser
1               5                   10                  15

<210> SEQ ID NO 7
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Val Asn Thr Ala Asn Ser Thr Gly Gly Ser Gly Ala Arg Arg Gly Val
1               5                   10                  15

Arg Val Ala Trp Arg Glu Pro Gly Arg Met Glu Leu Asn Met Pro His
            20                  25                  30

Gly Gly Ser Gly Lys
        35

<210> SEQ ID NO 8
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Val Asn Thr Ala Asn Ser Thr Gly Gly Ser Gly Ala Arg Arg Gly Val
1               5                   10                  15

Arg Val Ala Trp Arg Glu Pro Gly Arg Met Glu Leu Asn Met Pro His
            20                  25                  30

Gly Gly Ser Gly Lys
        35

<210> SEQ ID NO 9
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ser Thr Arg Ser Val Ser Ser Ser Ser Tyr Arg Arg Met Phe Gly Gly
1               5                   10                  15

Pro Gly Thr Ala Ser Lys
            20

<210> SEQ ID NO 10
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 10

Ser Thr Arg Ser Val Ser Ser Ser Tyr Arg Arg Met Phe Gly Gly
1               5                   10                  15

Pro Gly Thr Ala Ser Lys
            20

<210> SEQ ID NO 11
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Met Ala Leu Asp Ile Glu Ile Ala Thr Tyr Arg Lys Leu Leu Glu
1               5                   10                  15

Gly Glu Glu Ser Arg Ile Ser Gly Ser Gly Lys
            20                  25

<210> SEQ ID NO 12
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Lys Met Ala Leu Asp Ile Glu Ile Ala Thr Tyr Arg Lys Leu Leu Glu
1               5                   10                  15

Gly Glu Glu Ser Arg Ile Ser Gly Ser Gly Lys
            20                  25

<210> SEQ ID NO 13
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Arg Gly Val Arg Val Ala Trp Arg Glu Pro Gly Arg Met Glu Leu
1               5                   10                  15

Asn Met Pro His Gly Gly Ser Gly Lys
            20                  25

<210> SEQ ID NO 14
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Lys Val Arg Phe Leu Glu Gln Gln Asn Lys Ile Leu Leu Ala Glu Leu
1               5                   10                  15

Glu Gln Leu Lys Gly Gln Gly Lys
            20

<210> SEQ ID NO 15
<211> LENGTH: 24
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Lys Val Arg Phe Leu Glu Gln Gln Asn Lys Ile Leu Leu Ala Glu Leu
1               5                   10                  15

Glu Gln Leu Lys Gly Gln Gly Lys
            20

<210> SEQ ID NO 16
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Pro Lys Arg Asn Asp Gly Val Val Val Pro Arg Leu Leu Asp Ile
1               5                   10                  15

Thr Leu Arg Ala Tyr Asp Asn Arg Lys Ser Gly Lys
            20                  25

<210> SEQ ID NO 17
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Thr Arg Lys Arg Ile Arg Ile Gln Arg Gly Pro Gly Arg Ala Phe Val
1               5                   10                  15

Thr Ile Gly Gly Lys
            20

<210> SEQ ID NO 18
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Thr Arg Lys Ser Ile His Ile Gly Pro Gly Arg Ala Phe Tyr Thr Thr
1               5                   10                  15

Gly Gly Lys

<210> SEQ ID NO 19
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Arg Arg Gly Val His Val Gly Trp Arg Glu Pro Ser Phe Met Ala Leu
1               5                   10                  15

Ser Met Pro His Gly Gly Ser Gly Lys
```

-continued

```
                20                  25

<210> SEQ ID NO 20
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Arg Arg Gly Val Arg Val Ala Trp Arg Glu Pro Gly Arg Met Glu Leu
1               5                   10                  15

Asn Met Pro His Gly Gly Ser Gly Lys
            20                  25

<210> SEQ ID NO 21
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Arg Arg Gly Val Arg Val Ala Trp Arg Glu Pro Gly Arg Met Glu Leu
1               5                   10                  15

Asn Met Pro His Gly Gly Ser Gly Lys
            20                  25

<210> SEQ ID NO 22
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Trp Arg Glu Pro Ser Phe Met Ala Leu Ser
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Trp Arg Glu Pro Gly Arg Met Glu Leu Asn
1               5                   10

<210> SEQ ID NO 24
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(35)
<223> OTHER INFORMATION: D-amino acid

<400> SEQUENCE: 24
```

```
Cys Gly Ser Gly Gly Ser Gly Gly Ser Gly Ala Arg Arg Gly Val His
1               5                  10                  15

Val Gly Trp Arg Glu Pro Gly Arg Met Glu Leu Asn Met Pro His Gly
            20                  25                  30

Gln Pro Thr
        35

<210> SEQ ID NO 25
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Gly Ser Gly Tyr
1               5

<210> SEQ ID NO 26
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Gly Ser Ala Gly Ser Ala Ala Gly Ser Gly
1               5                  10

<210> SEQ ID NO 27
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Gly Ala Glu Ala Ala Ala Lys Glu Ala Ala Ala Lys Ala Gly
1               5                  10

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gly Gly Gly Gly
1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Gly Ser Gly
1
```

```
<210> SEQ ID NO 30
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Arg Gly Val His Val Gly
1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(2)
<223> OTHER INFORMATION: D-amino acid

<400> SEQUENCE: 31

Arg Arg Gly Val His Val Gly
1               5

<210> SEQ ID NO 32
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Lys Gly Arg Arg Gly Val His Val Gly
1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gly Gly Gly Gly Gly
1               5

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gly Gly Ser Gly Gly
1               5

<210> SEQ ID NO 35
<211> LENGTH: 5
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Ser Gly Gly Ser Gly
1               5

<210> SEQ ID NO 36
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Ser Gly Ser Gly Ser
1               5

<210> SEQ ID NO 37
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Gly Ser Gly Gly Ser Lys
1               5

<210> SEQ ID NO 38
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gly Ser Gly Gly Ser Gly Gly Ser Gly
1               5

<210> SEQ ID NO 39
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gly Gly Ser Gly Gly Ser Gly Gly
1               5

<210> SEQ ID NO 40
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gly Gly Arg Arg Gly Val His Val Gly
1               5
```

```
<210> SEQ ID NO 41
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Cys Gly Ser Gly Gly
1               5

<210> SEQ ID NO 42
<211> LENGTH: 2
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Gly Gly
1

<210> SEQ ID NO 43
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Cys Gly Arg Arg Gly Val His Val Gly
1               5

<210> SEQ ID NO 44
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Cys Ala Arg Arg Gly Val His Val Gly
1               5

<210> SEQ ID NO 45
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Arg Arg Arg Arg Arg Arg Arg Arg Arg
1               5

<210> SEQ ID NO 46
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (1)..(9)
<223> OTHER INFORMATION: D-amino acid

<400> SEQUENCE: 46

Arg Arg Arg Arg Arg Arg Arg Arg Arg
1               5

<210> SEQ ID NO 47
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Thr Arg Ser Phe Cys Thr Asp Trp Pro Ala His Lys Ser Cys Lys Pro
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Arg Gln Met Glu Asp Ile Cys Leu Pro Arg Trp Gly Cys Leu Trp Gly
1               5                   10                  15

Asp

<210> SEQ ID NO 49
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 49

Xaa Ala Gly Lys Lys Pro Arg Val Thr Val Thr Asn Val Phe Leu Tyr
1               5                   10                  15

Asn Arg Pro Leu Asn Ser Thr Glu
            20

<210> SEQ ID NO 50
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 50

Xaa Ala Gly Lys Lys Pro Arg Val Thr Val Thr Asn Val Phe Leu Tyr
1               5                   10                  15
```

Asn Arg Pro Leu Asn Ser Thr Glu
            20

<210> SEQ ID NO 51
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 51

Xaa Ala Gly Lys Lys Pro Ser Val Thr Val Thr Asn Val Phe Leu Tyr
1               5                   10                  15

Asn Arg Pro Leu Asn Ser Thr Glu
            20

<210> SEQ ID NO 52
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Ahx

<400> SEQUENCE: 52

Xaa Ala Gly Lys Lys Pro Ser Val Thr Val Thr Asn Val Phe Leu Tyr
1               5                   10                  15

Asn Arg Pro Leu Asn Ser Thr Glu
            20

<210> SEQ ID NO 53
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Pro Lys Arg Asn Asp Gly Val Val Val Pro Arg Leu Leu Asp Ile
1               5                   10                  15

Thr Leu Arg Ala Tyr Asp Asn Arg Lys Ser Gly Lys
            20                  25

<210> SEQ ID NO 54
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Thr Arg Lys Arg Ile Arg Ile Gln Arg Gly Pro Gly Arg Ala Phe Val
1               5                   10                  15

Thr Ile Gly Gly Lys
            20

<210> SEQ ID NO 55
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Thr Arg Lys Ser Ile His Ile Gly Pro Gly Arg Ala Phe Tyr Thr Thr
1               5                   10                  15

Gly Gly Lys

<210> SEQ ID NO 56
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Cys Gly Lys Asn Leu Gln Glu Ala Glu Trp Tyr Lys Ser Lys Phe
1               5                   10                  15

Ala Asp Leu Ser Glu Ala Ala Asn Arg
            20                  25

<210> SEQ ID NO 57
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Gly Ser Glu Ala Ala Asn Arg Asn Asn Asp Ala Leu Arg Gln Ala
1               5                   10                  15

Lys Gln Glu Ser Thr Glu Tyr Arg Arg
            20                  25

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Cys Gly Gly Lys Thr Val Glu Thr Arg Asp Gly Gln Val Ile Asn Glu
1               5                   10                  15

Thr Ser Gln His His Asp Asp Leu Glu
            20                  25

<210> SEQ ID NO 59
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Lys Met Ala Leu Asp Ile Glu Ile Ala Thr Tyr Arg Lys Leu Leu Glu
1               5                   10                  15

Gly Glu Glu Ser Arg Ile Ser Gly Cys
            20              25
```